United States Patent
Sabir et al.

(10) Patent No.: US 8,660,981 B2
(45) Date of Patent: Feb. 25, 2014

(54) SYSTEM AND METHOD FOR HIERARCHICAL STREAM PROCESSING

(75) Inventors: Kenneth Sabir, Marrickville (AU); David Lowe, Ultimo (AU)

(73) Assignee: International Business Machines Corporation, Armonk, NY (US)

(*) Notice: Subject to any disclaimer, the term of this patent is extended or adjusted under 35 U.S.C. 154(b) by 356 days.

(21) Appl. No.: 13/212,449

(22) Filed: Aug. 18, 2011

(65) Prior Publication Data

US 2013/0046858 A1 Feb. 21, 2013

(51) Int. Cl.
*G06F 15/00* (2006.01)
*G06F 15/18* (2006.01)

(52) U.S. Cl.
USPC .................................................. 706/62

(58) Field of Classification Search
USPC .................................................. 706/62
See application file for complete search history.

(56) References Cited

U.S. PATENT DOCUMENTS

| | | | |
|---|---|---|---|
| 6,944,785 B2 | 9/2005 | Gadir et al. | |
| 2004/0143725 A1 | 7/2004 | Addison | |
| 2005/0240542 A1 | 10/2005 | Curtis | |
| 2006/0122952 A1 | 6/2006 | Hinchey et al. | |
| 2007/0179944 A1 | 8/2007 | Van Dyke Parunak et al. | |
| 2010/0153082 A1 | 6/2010 | Newman et al. | |

FOREIGN PATENT DOCUMENTS

| | | | |
|---|---|---|---|
| WO | 2010057614 A1 | 5/2010 | |
| WO | 2010060923 A1 | 6/2010 | |

OTHER PUBLICATIONS

Mittal et al., "LOCI—Local Clustering Service for Large Scale Wireless Sensor Networks," Department of Computer & Information Science, http://www.google.co.in/webhp?sourceid=navclient-ff#hl=en&source=hp&biw=1280&bih=585&q=LOCI-LOCAL+CLUSTERING&btnG=Google+Search&oq=LOCI-LOCAL+CLUSTERING&aq=f&aqi=aqi=aql=&gs_sm=s&gs_upl=22981147791012112010114101014021199012-2.2.2&fp=20c7f5b7c64c1a51; downloaded Jun. 2, 2011, pp. 1-35.

Prokopenko et al., "On Connectivity of Reconfigurable Impact Networks in Ageless Aerospace Vehicles," Robotics and Autonomous Systems 53, www.sciencedirect. com, (2005) pp. 36-58.

Tempesti et al., "Bio-Inspired Computing Architectures: The Embryonics approach," proceedings of the Seventh International Workshop on Computer Architecture for Machine Perception Jul. 4-6, 2005, pp. 1-8.

Lakshmanan et al., "Biologically-Inspired Distributed Middleware Management for Stream Processing Systems," 2006, pp. 223-241.

(Continued)

*Primary Examiner* — Kakali Chaki
*Assistant Examiner* — Vincent Gonzales
(74) *Attorney, Agent, or Firm* — Holland & Knight LLP; Brian J. Colandreo, Esq.; Jeffrey T. Placker, Esq.

(57) ABSTRACT

A method, computer program product, and system for de-centralized stream processing is provided. The method may include providing a plurality of processing nodes each of said processing nodes configured to transmit and receive a stream of data. The method may also include providing a genome including a hierarchical set of tasks that represent a hierarchical functional decomposition of one or more problem scenarios. The method may further include identifying, at each of the processing nodes, one or more tasks for a first genome level. The method may additionally include differentiating, at one or more of the plurality of processing nodes, into one or more tasks, based upon, at least in part, the first genome level. The method may further include grouping a plurality of the processing nodes together to achieve a power level. The method may also include activating a second genome level once the power level has been reached. The method may further include repeating until one or more of the nodes differentiates into a further genome level.

20 Claims, 22 Drawing Sheets

(56) References Cited

OTHER PUBLICATIONS

Kwon et al., "DANS: Decentralized, Autonomous, and Network-Wide Service Delivery and Multimedia Workflow Processing," MM '06 Oct. 23-26, 2006, pp. 1-10.

Balazinska et al., "The Medusa Distributed Stream-Processing System," MIT Computer Science and Artificial Intelligence Lab, http://nms.lcs.mit.edu/projects/medusa/, pp. 1-7.

Zambonelli et al., "Spray Computers: Exploration sin Self-Organization," Journal of Pervasive and Mobile Computing, vol. 1, No. 1., 2004, pp. 1-20.

Mamei et al., "Self-Organizing Spatial Shapes in Mobile Particles: The TOTA Approach," http://www.ia.urjc.es/-matteo/resources/papers/esoa2004.pdf; 2004, pp. 1-15.

George et al., "A Biological Program Model for Self-Healing," Department of Computer Science, Oct. 2003, pp. 1-10.

Gierer et al., "A Theory of Biological Pattern Formation," Kybernetik 12, 1972, Sep. 8, 1972, pp. 30-39.

Guo et al., "A Cellular Mechanism for Multi-Robot Construction Via Evolutionary Multi-Objective Optimization of a Gene Regulatory Network," Bio Systems, Journal of Biological and Information Processing Sciences, ISSN 0303-2647, vol. 98, No. 3, 2009, pp. 127-203.

Ren et al., "Biologically Inspired Approaches for Wireless Sensor Networks," Proceedings of the 2006 IEEE International Conference on Mechatronics and Automation, Jun. 25-28, 2006, Luoyang, China, pp. 762-768.

Neglia et al., "Evaluating Activator-Inhibitor Mechanisms for Sensors Coordination," Bionetics '07 Dec. 10-13, 2007, Budapest, Hungary, 5 pages.

Ortega et al., "Reliability Analysis in Self-Repairing Embryonic Systems," Department of Electronics University of York; pp. 1-9, Proc. of the First NASA/DoD WOrkshop on Evolvable Hardware, IEEE 1999.

Stephens, "A Survey of Stream Processing," Acta Informatica, vol. 34, 1997, pp. 491-541.

Anderson, "BOINC: A System for Public-Resource Computing and Storage," Fifth IEEE/ACM International Workshop on Grid Computing, 1999, pp. 4-10.

Kahn, "The Semantics of a Simple Language for Parallel Programming," Information Processing '74: Proceedings of the IFIP Congress, J.S. Rosenfeld, New York, NY, North-Holland, 1974, pp. 471-475.

Kahn et al., "Coroutines and Networks of Parallel Processes, Information Processing," Proceedings of IFIP Congress, 1977, pp. 993-998.

Rea et al., "IBM InfoSphere Streams," Proceedings of the 2009 Conference of the Center for Advanced Studies on Collaborative Research—CASCON '09, 2009, p. 311.

Gedik et al., "SPADE: The System S Declarative Stream Processing Engine," 2008 ACM SIGMOD International Conference on Management of Data, 2008, pp. 1123-1134.

Hirzel et al., "IBM Research Report: SPL Stream Processing Language Specification Language Specification," vol. 24987, 2009; pp. 1-53.

Reeuwijk et al., "Maestro: A Self-Organizing Peer-to-Peer Dataflow Framework Using Reinforcement Learning," Context, 2009, pp. 187-196.

Miorandi et al., "Embryonic Models for Self-Healing Distributed Services," Bionetics 2009; 4th International Conference on Bio-Inspired Models of Network, Information, and Computing Systems, Avignon, France, 2009; pp. 152-166.

Meinhardt, "Models of Biological Pattern Formation," London: Academic Press, 1982, pp. 1-211.

Nagpal, "A Catalog of Biologically-Inspired Primitives for Engineering Self-Organization Primitives for Robust Local Behavior," Most, 2004, pp. 53-62.

However, if stem cells were also part of the minimum requirements calculation, then redundancy may be built in. In this case, there is only one type of role the MSC may differentiate into. There are called Level 0 Stem Cells (S). (N) represents a new cell from a stem cell.

SYSTEM AND METHOD FOR HIERARCHICAL STREAM PROCESSING

BACKGROUND OF THE INVENTION

The growth of real-time digital systems, wireless sensor networks, and distributed processing has seen the emergence of a class of applications that focus on the continuous analysis of real-time data. This data takes numerous forms, for example, audio, video, images, text, sensor data, and is typically subjected to complex processing. Stream processing is a distributed programming paradigm that has been shown to be suitable for processing massive amounts of continuous data in real-time. It is based on the application of a series of processing operators to each element in a continuous data set (or stream) rather than the sequential processing of each data item.

While stream processing need not be implemented in a distributed fashion, it is in this domain that it is most often considered. The flow of data in a stream processing system can be represented in a dataflow graph where each node in the graph models a processing task, or role, that may produce output streams of continuous data from the given input streams. Each of the processing roles would then be deployed to a set of (possibly distributed) processors. The existing literature on stream processing has mainly focused on a centralized application manager that can allocate each processing role to a suitable (possibly distributed) processor. A centralized determination of the role allocation is effective in many scenarios and should facilitate a global optimization of the role allocation.

However, as the volume of data, the number of processors, and the complexity of the dataflow graph all increase, a centralized approach will potentially suffer scalability issues. This problem will be amplified if the number of processing nodes is constantly changing, which may be the case if the processing nodes are drawn from a volatile resource pool. Typical scenarios where this may arise would be stream processing systems that leverage the processor capability within a large network of mobile phones, wireless sensors or the spare capacity within a network of fixed computers (as with the Berkeley Open Infrastructure for Network Computing "BOINC" architecture).

BRIEF SUMMARY OF THE INVENTION

In a first embodiment, a method for de-centralized stream processing is provided. The method may include providing a plurality of processing nodes each of said processing nodes configured to transmit and receive a stream of data. The method may also include providing a genome including a hierarchical set of tasks that represent a hierarchical functional decomposition of one or more problem scenarios. The method may further include identifying, at each of the processing nodes, one or more tasks for a first genome level. The method may additionally include differentiating, at one or more of the plurality of processing nodes, into one or more tasks, based upon, at least in part, the first genome level. The method may further include grouping a plurality of the processing nodes together to achieve a power level. The method may also include activating a second genome level once the power level has been reached. The method may further include repeating until one or more of the nodes differentiates into a further genome level.

One or more of the following features may be included. In some embodiments, grouping may utilize, at least in part, quorum sensing. In some embodiments, each of the plurality of processing nodes may be in communication with a subsection of a genome. In some embodiments, reaching a power level may be associated with obtaining a desired amount of processing power for a particular task. In some embodiments, each of the plurality of processing nodes may maintain one or more morphogen levels associated with its parent processing node. In some embodiments, the morphogen levels may be associated with at least one of activation and inhibition. The method may further include load balancing between one or more of the plurality of processing nodes.

In a second embodiment, a computer program product may reside on a computer readable storage medium and may have a plurality of instructions stored on it. When executed by a processor, the instructions may cause the processor to perform operations including providing a plurality of processing nodes each of said processing nodes configured to transmit and receive a stream of data. Operations may also include providing a genome including a hierarchical set of tasks that represent a hierarchical functional decomposition of one or more problem scenarios. Operations may further include identifying, at each of the processing nodes, one or more tasks for a first genome level. Operations may additionally include differentiating, at one or more of the plurality of processing nodes, into one or more tasks, based upon, at least in part, the first genome level. Operations may further include grouping a plurality of the processing nodes together to achieve a power level. Operations may also include activating a second genome level once the power level has been reached. Operations may further include repeating until one or more of the nodes differentiates into a further genome level.

One or more of the following features may be included. In some embodiments, grouping may utilize, at least in part, quorum sensing. In some embodiments, each of the plurality of processing nodes may be in communication with a subsection of a genome. In some embodiments, reaching a power level may be associated with obtaining a desired amount of processing power for a particular task. In some embodiments, each of the plurality of processing nodes may maintain one or more morphogen levels associated with its parent processing node. In some embodiments, the morphogen levels may be associated with at least one of activation and inhibition. Operations may further include load balancing between one or more of the plurality of processing nodes.

In a third embodiment, a computing system is provided. The computing system may include at least one processor and at least one memory architecture coupled with the at least one processor. The computing system may also include a first software module executable by the at least one processor and the at least one memory architecture, wherein the first software module may be configured to provide a plurality of processing nodes each of said processing nodes configured to transmit and receive a stream of data. The computing system may also include a second software module executable by the at least one processor and the at least one memory architecture, wherein the second software module may be configured to provide a genome including a hierarchical set of tasks that represent a hierarchical functional decomposition of one or more problem scenarios. The computing system may also include a third software module executable by the at least one processor and the at least one memory architecture, wherein the third software module may be configured to identify, at each of the processing nodes, one or more tasks for a first genome level. The computing system may also include a fourth software module executable by the at least one processor and the at least one memory architecture, wherein the fourth software module may be configured to differentiate, at one or more of the plurality of processing nodes, into one or more tasks, based upon, at least in part, the first genome level. The computing system may also include a fifth software module executable by the at least one processor and the at least one memory architecture, wherein the fifth software module may be configured to group a plurality of the processing nodes together to achieve a power level. The computing system may also include a sixth software module executable by the at least one processor and the at least one memory architecture, wherein the sixth software module may be configured to activate a second genome level once the power level has been reached. The computing system may also include a seventh software module executable by the at least one processor and the at least one memory architecture, wherein the seventh software module may be configured to repeat until one or more of the nodes differentiates into a further genome level.

One or more of the following features may be included. In some embodiments, grouping may utilize, at least in part, quorum sensing. In some embodiments, each of the plurality of processing nodes may be in communication with a subsection of a genome. In some embodiments, reaching a power level may be associated with obtaining a desired amount of processing power for a particular application. In some embodiments, each of the plurality of processing nodes may maintain one or more morphogen levels associated with its parent processing node. In some embodiments, the morphogen levels may be associated with at least one of activation and inhibition. The computing system may further include one or more software modules configured to load balance between one or more of the plurality of processing nodes.

The details of one or more implementations are set forth in the accompanying drawings and the description below. Other features and advantages will become apparent from the description, the drawings, and the claims.

DETAILED DESCRIPTION OF THE INVENTION

Figure 1:
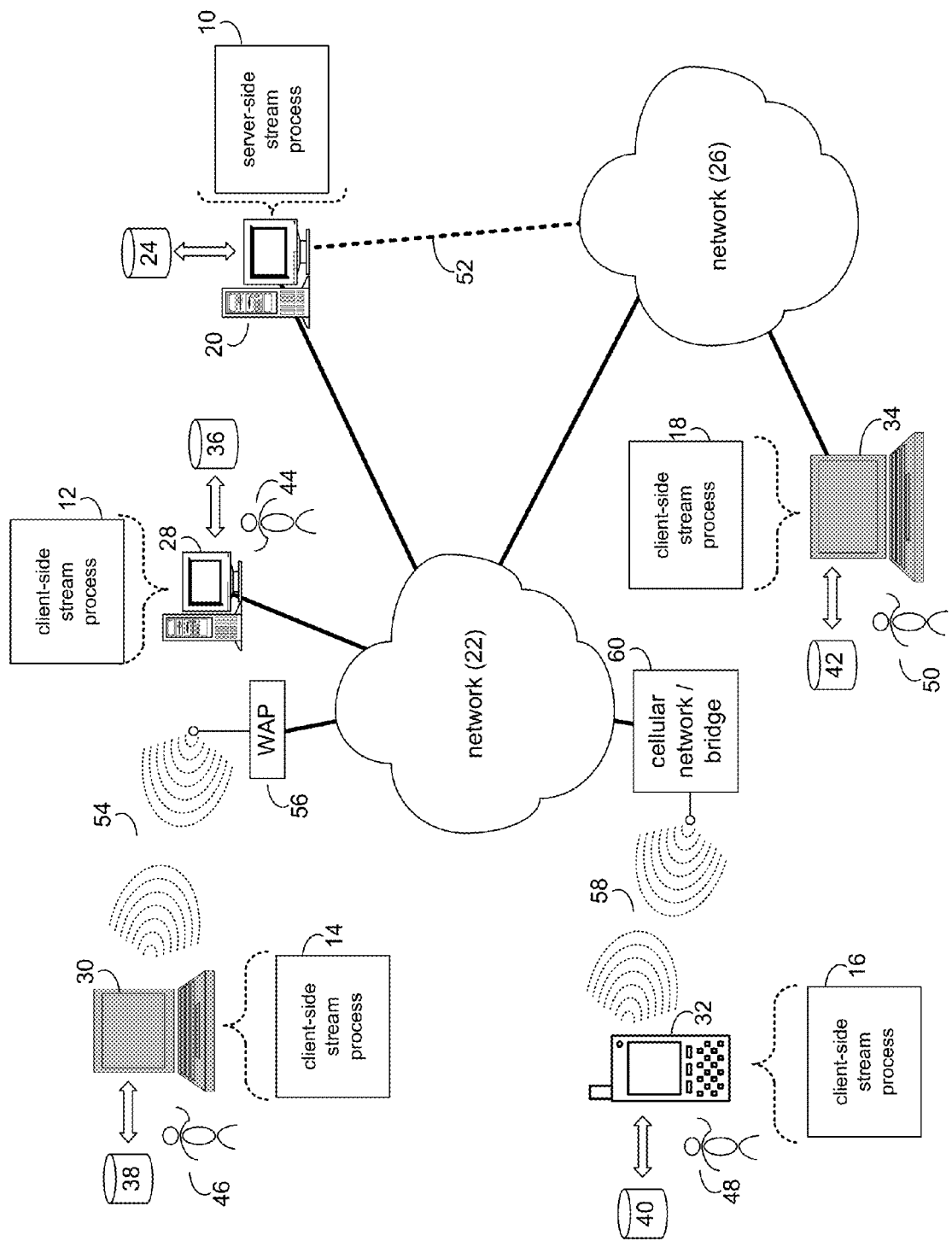
FIG. 1 is a diagrammatic view of a stream process coupled to a distributed computing network in accordance with the present disclosure.
Figure 2:
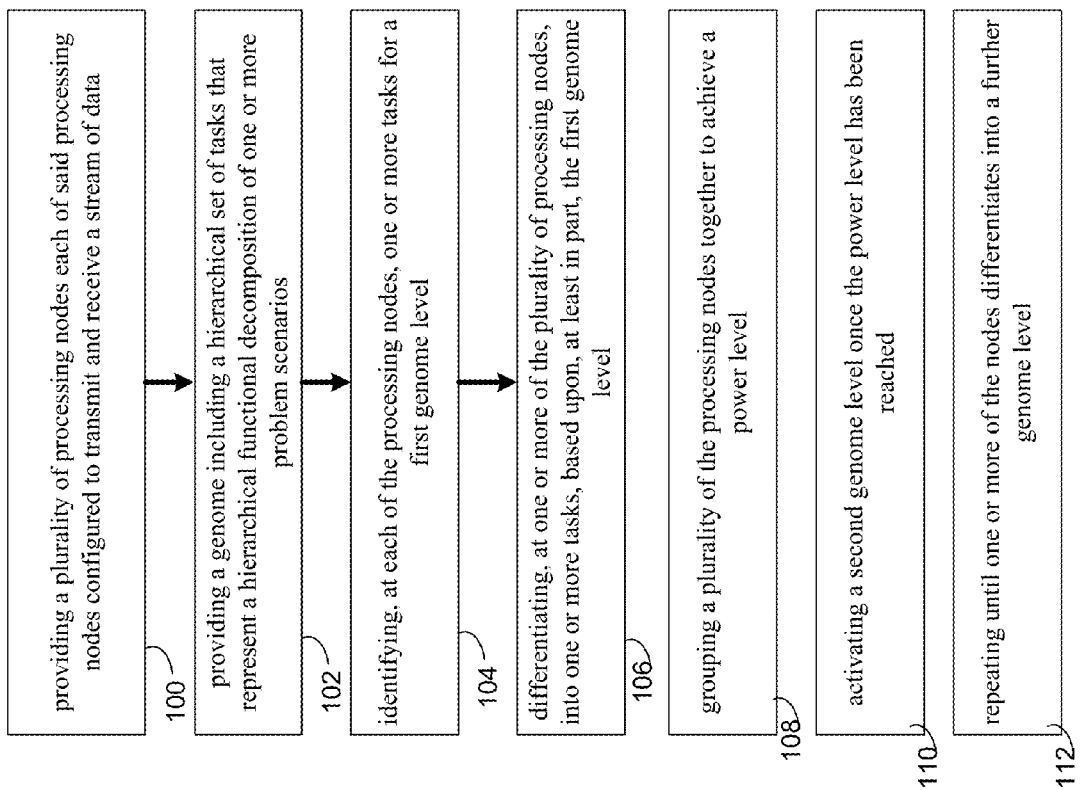
FIG. 2 is a flowchart of the hierarchical stream process of FIG. 1 in accordance with the present disclosure.

Referring to FIGS. 1 & 2, there is shown an embryonic stream process 10. As will be discussed below, embryonic stream process 10 may provide a plurality of processing nodes each of said processing nodes configured to transmit and receive a stream of data. Embryonic stream process 10 may add one or more new processing nodes to the computing system. Embryonic stream process 10 may determine a source node based upon, at least in part, an activation level being above or below a particular threshold. For each of the one or more added processing nodes, embryonic stream process 10 may automatically determine an appropriate role, based upon, at least in part, a neighboring processing node.

The term "genome" as used herein may refer to the set of all available roles that a node can differentiate into. The entire set of roles may describe all aspects of processing that the system will perform. The genome may also include the interrelations between the roles. For example, the output of Role A may be the input of Role B. The genome may also include any restrictions or promotions regarding the differentiation process for each node. For example, the genome may know if Role A requires input from a camera on a node. If a particular node does not have a camera, then it should never differentiate into Role A.

The term "role" or "task" as used herein may refer to a process that modifies (e.g., none to many) streaming input data to produce (e.g., none to many) streaming output data. The set of all the roles of a system may describe all of the processing that occurs on the system.

The term "node" or "cell" as used herein may refer to a processing unit that may include a CPU, memory, I/O, etc. Some possible examples of nodes may include, but are not limited to, sensors in a wireless sensor network, mobile phones, computers, or Micro Electronic Mechanical Systems (MEMS).

The term "stem cell" may refer to a node that may refrain from differentiating into a particular role. Instead, it may remain undifferentiated waiting for a nearby node to fail. When the neighbor failure occurs, the stem cell may then differentiate to the role that had the error, providing redundancy.

The term "activation" as used herein may refer to a variable that may represent a virtual chemical that is produced self-catalytically. Activation may be produced, diffused and decayed over time. The amount of activation produced may be proportional to the current activation squared and may be inversely proportional to the amount of inhibition present.

Activation may diffuse slower then inhibition meaning its range of influence through diffusion may be limited when compared to the range of same amount of inhibition diffused.

The term "inhibition" may refer to a variable that may represent a virtual chemical that may be produced proportionally to the current activation squared. Inhibition may be produced, diffused and decayed over time. Inhibition may diffuse more rapidly then activation so it may reach a greater number of roles through diffusion when compared to range of activation diffusion.

For the following discussion, server-side processes 10 will be described for illustrative purposes. It should be noted that client-side process 12 may be incorporated into server-side process 10 and may be executed within one or more applications that allow for communication with client-process 12. However, this is not intended to be a limitation of this disclosure, as other configurations are possible (e.g., stand-alone, client-side automated testing processes and/or stand-alone server-side automated testing processes.) For example, some implementations may include one or more of client-side processes 12, 14, 16, 18 in place of or in addition to server-process 10.

The embryonic stream process may be a server-side process (e.g., server-side process 10), a client-side process (e.g., client-side process 12, client-side process 14, client-side process 16, or client-side process 18), or a hybrid server-side/client-side process (e.g., the combination of server-side automated testing process 10 and one or more of client-side processes 12, 14, 16, 18).

Server-side embryonic stream process 10 may reside on and may be executed by server computer 20, which may be connected to network 22 (e.g., the Internet or a local area network). Examples of server computer 20 may include, but are not limited to: a personal computer, a server computer, a series of server computers, a mini computer, and/or a mainframe computer. Server computer 20 may be a web server (or a series of servers) running a network operating system, examples of which may include but are not limited to: Microsoft® IIS, Novell® Web Server, or Apache® Web Server, for example.

The instruction sets and subroutines of server-side embryonic stream process 10, which may be stored on storage device 24 coupled to server computer 20, may be executed by one or more processors (not shown) and one or more memory architectures (not shown) incorporated into server computer 20. Storage device 24 may include but is not limited to: a hard disk drive; a tape drive; an optical drive; a RAID array; a random access memory (RAM); and a read-only memory (ROM).

Server computer 20 may execute a web server application that allows for access to server computer 20 (via network 22) using one or more protocols, examples of which may include but are not limited to HTTP (i.e., HyperText Transfer Protocol), SIP (i.e., session initiation protocol), and the Lotus® Sametime® VP protocol. Network 22 may be connected to one or more secondary networks (e.g., network 26), examples of which may include but are not limited to: a local area network; a wide area network; or an intranet, for example.

Client-side processes 12, 14, 16, 18 may reside on and may be executed by client electronic devices 28, 30, 32, and/or 34 (respectively), examples of which may include but are not limited to personal computer 28, laptop computer 30, a data-enabled mobile telephone 32, notebook computer 34, personal digital assistant (not shown), smart phone (not shown) and a dedicated network device (not shown), for example. Client electronic devices 28, 30, 32, 34 may each be coupled to network 22 and/or network 26 and may each execute an operating system, examples of which may include but are not limited to those described above.

The instruction sets and subroutines of client-side processes 12, 14, 16, 18, which may be stored on storage devices 36, 38, 40, 42 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Storage devices 36, 38, 40, 42 may include but are not limited to: hard disk drives; tape drives; optical drives; RAID arrays; random access memories (RAM); read-only memories (ROM); compact flash (CF) storage devices; secure digital (SD) storage devices; and memory stick storage devices.

Client-side processes 12, 14, 16, 18 and/or server-side embryonic stream process 10 may be processes that run within (e.g., are part of) a software testing system and/or application. Alternatively, client-side embryonic stream processes 12, 14, 16, 18 and/or server-side embryonic stream process 10 may be stand-alone applications that work in conjunction with the software testing system and/or application. One or more of client-side processes 12, 14, 16, 18 and server-side embryonic stream process 10 may interface with each other (via network 22 and/or network 26).

Users 44, 46, 48, 50 may access server-side embryonic stream process 10 directly through the device on which the client-side process (e.g., client-side processes 12, 14, 16, 18) is executed, namely client electronic devices 28, 30, 32, 34, for example. Users 44, 46, 48, 50 may access server-side embryonic stream process 10 directly through network 22 and/or through secondary network 26. Further, server computer 20 (i.e., the computer that executes server-side embryonic stream process 10) may be connected to network 22 through secondary network 26, as illustrated with phantom link line 52.

The various client electronic devices may be directly or indirectly coupled to network 22 (or network 26). For example, personal computer 28 is shown directly coupled to network 22 via a hardwired network connection. Further, notebook computer 34 is shown directly coupled to network 26 via a hardwired network connection. Laptop computer 30 is shown wirelessly coupled to network 22 via wireless communication channel 54 established between laptop computer 30 and wireless access point (i.e., WAP) 56, which is shown directly coupled to network 22. WAP 56 may be, for example, an IEEE 802.11a, 802.11b, 802.11g, 802.11n, Wi-Fi, and/or Bluetooth device that is capable of establishing wireless communication channel 54 between laptop computer 30 and WAP 56. Data-enabled mobile telephone 32 is shown wirelessly coupled to network 22 via wireless communication channel 58 established between data-enabled mobile telephone 32 and cellular network/bridge 60, which is shown directly coupled to network 22.

As is known in the art, all of the IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. As is known in the art, Bluetooth is a telecommunications industry specification that allows e.g., mobile phones, computers, and personal digital assistants to be interconnected using a short-range wireless connection.

The Stream Process

In some embodiments, stream process 10 may provide a plurality of processing nodes each of said processing nodes configured to transmit and receive a stream of data. Stream process 10 may add one or more new processing nodes to the computing system. Stream process 10 may determine a source node based upon, at least in part, an activation level being above or below a particular threshold. For each of the one or more added processing nodes, stream process 10 may automatically determine an appropriate role, based upon, at least in part, a neighboring processing node.

As discussed above, the flow of data in a stream processing system may be represented in a dataflow graph where each node in the graph models a processing task, or role, that may produce output streams of continuous data from the given input streams. Each of the processing roles would then be deployed to a set of (possibly distributed) processors. The existing literature on stream processing has mainly focused on a centralized application manager that can allocate each processing role to a suitable (possibly distributed) processor. A centralized determination of the role allocation is effective in many scenarios and should facilitate a global optimization of the role allocation.

In some embodiments of the present disclosure, role allocation may be distributed, thus allowing for a particular system to become significantly more scalable, robust and autonomic. The teachings of the present disclosure allow for each processing node to be able to autonomously determine its optimal role selection, within constraints that guarantee optimized dataflow graphs, thus leading to a simpler and more scalable architecture. This would be particularly suitable to massive scale networks where node availability may be dynamic and non-deterministic. This problem of creating a distributed dataflow may become more important as the number of digital devices, along with the amount of data they provide, increases worldwide. Some potential applications of a distributed role allocation may include, but are not limited to, smart sensors, micro-electro-mechanical systems (MEMS), or swarming robots processing streaming data (video, audio and intelligence) where each node is autonomous yet contributing to the clustered computing power. The teachings of the present disclosure may also be applied to existing stream applications on mainframes where nodes can self-organize to utilize shared memory, thus gaining the benefits of robustness and scalability due to the distributed role allocation.

In some embodiments, when new nodes (e.g., sensors, mobile phones, computers, etc.) are added to the system, they may automatically learn what role to take on (e.g., by looking at its neighboring nodes) in order to be of the most benefit to the system. Since a stream application may be represented by a data flow graph, for an embryonic solution this graph is part of the 'genome' of the system. In some embodiments, the genome may contain the relationships between roles and each roles requirements (e.g. a particular role might require a camera sensor on the node). In some embodiments, the genome may refer to the set of all available processors or elements for a particular application. Each node in the system may know the whole genome and may differentiate into a suitable role to maximize efficiency based on what roles are available on neighboring nodes.

In some embodiments, in order to separate the roles among the nodes, a technique called morphogenesis may be used. Morphogenesis may be used to describe how cells can autonomously differentiate with global knowledge for biological pattern generation. Morphogenesis may be used to make sure the roles are separated while influencing neighbors to become desirable roles to improve efficiency. The embryonic stream process described herein will be robust and scalable as there is no central server so it will have no single point of failure.

In some embodiments, morphogenesis may allow for autonomous nodes to separate without any central control. Consider the spots on a leopard, for example, how a hair follicle cell knows whether to be light or dark based on information gathered from neighboring cells through the chemical diffusion processes. A theory for this process is called autocatalysis and long range inhibition and is based on reaction-diffusion mechanisms. The centre cell of a dark spot on a leopard's skin might be thousands of cells away from the edge of the spot, so a process of a decreasing gradient of chemicals called morphogens are passed from the centre cell so that all cells know how far away they are from the source based on the morphogen concentration at a given node.

The equations for morphogenic behavior for spacial separation are described in H. Meinhardt, Models of Biological Pattern Formation, London: Academic Press, 1982. The two primary chemicals may include activation and inhibition.

In some embodiments, the following activation-inhibition equations may be used:

$$\frac{\partial a}{\partial t} = \frac{sa^2 + C_a}{b} - d_a a + D_a \frac{\partial^2 a}{\partial x^2} \qquad \text{EQN 1}$$

$$\frac{\partial b}{\partial t} = sa^2 - d_b b + D_b \frac{\partial^2 b}{\partial x^2} \qquad \text{EQN 2}$$

In equations 1 and 2 above, "a" may refer to the activation chemical concentration and "b" may refer to the inhibition chemical concentration. "Ca" refers to a small constant activation production, so the activation may become reignited in quiet sections of the graph. The rate of decay is given by "da" and "db" for the activation and inhibition respectively. The morphogens are diffused between neighbors with "Da" and "Db" being the constants for the laplacian diffusion transformation of the activation and inhibition. The source density, "s", may be constant or variable. As used herein, the term "autocatalysis" may refer to the activation morphogen that is created on a source node or a likely source node contender, which will further establish its status as being a source node gaining high activation through a process of self-activation.

Figure 3:
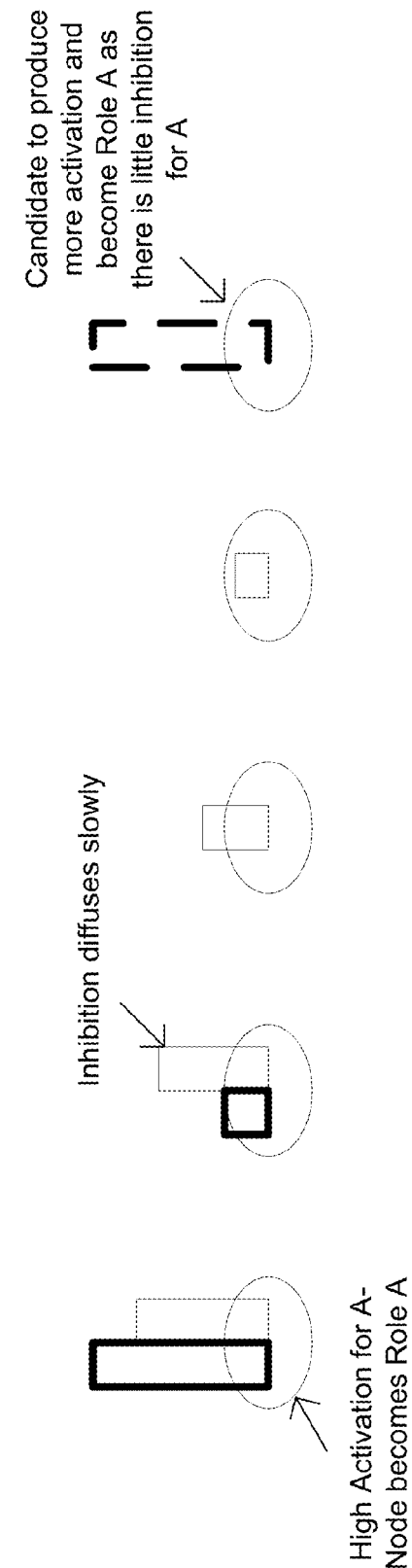
FIG. 3 depicts a diagram showing the concept of morphogenic spatial separation in accordance with the present disclosure.

Referring now to FIG. 3, an embodiment 300 is provided depicting the basic principals for spatial separation from morphogenesis. In this particular embodiment, the activation level is indicated by the bold outline. When the activation is above a particular threshold, the node may becomes Role A. In this way, process 10 may automatically determine an appropriate role, based upon, at least in part, a neighboring processing node. As discussed herein, automatically determining may include analyzing the activation level and an inhibition level.

In some embodiments, applying autocatalysis and long range inhibition to a set of nodes may produce a subset of source nodes that are geographically evenly spaced. A node may become a source node when its activation is above a given threshold. In some embodiments, an approach for solving differentiation in distributed dataflow is to allocate a separate morphogen pair of activation and inhibition for each possible role in the dataflow. In this way, the morphogens may then be influenced not only by its own and neighboring levels of activation and inhibition, but also by the morphogens of other roles in the node. This may result in multiple morphogens interacting with each other on the same node to influence desired inputs and outputs in the local neighborhood to find an optimal solution for a dataflow graph role distribution.

In some embodiments, one or more additional variables may be included to complement the existing morphogen equations (i.e., EQN 1 and EQN 2), namely desire, power and global inhibition. Each possible role on a node will have a value for activation, inhibition, desire and power, while global inhibition is also maintained for the node but it is not role specific. Also, the source density of equations (2a, 2b) will be modified to utilize these new variables.

$$s_r = S_c \frac{q_r}{p_r} \qquad \text{EQN 3}$$

where $s_r$ is source density for role r, Sc is a constant, $q_r$ is desire, and $p_r$ is power of role r. In words, the source density for a role is proportional to how much desire there is for that role over how much existing power is already present.

Desire (EQN 4) may cover the inter-node influence required to promote desired roles on neighboring nodes.

$$\frac{\partial q_r}{\partial t} = -d_q q_r + D_q \frac{\partial^2 q_r}{\partial x^2} \qquad \text{EQN 4}$$

Where $$\frac{\partial^2 q_r}{\partial x^2} = \frac{1}{|N_n|} \Sigma_{n_z \in N_n}(q_{z,r} - q_{n,r}). \qquad \text{EQN 5}$$

In some embodiments, the desire from neighbor z is given by $q_{z,r}$. It may be calculated based on the neighbor's activation of each of the supporting roles minus the existing power ($p_{z,r}$) of the role in question. This may be demonstrated by, $$q_{z,r} = \Sigma_{t \in R_r}(a_{z,t} - p_{z,r})(|R_r|)^{-1/2} \qquad \text{EQN 6}$$

Here, Rr is the set of roles that are role-neighbors (inputs and outputs) of role r in the genome. The activation for neighbor z of role t is given by $a_{z,t}$ and $p_{z,r}$ is its power for role r. The desire value can be calculated on the neighboring nodes (Nn) and diffused immediately without these nodes needing to store it locally. The nodes in Nn will receive their own desire morphogens from their own diffusion process. Otherwise, a node will increase the desire for its inputs and outputs on itself, potentially confusing its main role. To explain this further, we shall revisit FIG. 4 as an example.

In some embodiments, some nodes in a system will become role A due to a high concentration of activation for A. These nodes can in turn distribute extra desire for Role B, as it is beneficial to have a B node close to an A node. The A nodes will not increase the desire for B on itself, but only on their neighbors. Likewise, the B nodes will distribute desire for both A and C, covering the desired inputs and the outputs of Role B. Load balancing could also come into the desire (EQN 4) equation since if a B node is getting overloaded, that means that there is a high demand for B in that area, and so it can send extra desire to get support for its excess demand. The neighbors desire, $q_z$, is also partially normalized against roles with more connections without favoring the endpoints, which would occur if it was completely normalized.

2) Power

In some embodiments, power may refer to a linear measure of proximity to a source activation as opposed to inhibition that is the square of activation. Power defuses more slowly than activation giving it a wider influence. The power equation is similar to the source density equations (2g,2h). However, since source density has been changed to work for multiple role morphogens (EQN 3), and $p_r$ is now inversely proportional to source density (EQN 3), this variable is renamed to be power.

$$\frac{\partial p_r}{\partial t} = Y(a_r - p_r) - d_p p_r + D_p \frac{\partial^2 p_r}{\partial x^2} \qquad \text{(3e)} \qquad \text{EQN 7}$$

3) Global Inhibition

In some embodiments, with multiple morphogens acting on the one node, there is the chance that a node could become highly active in multiple roles, hence inhibiting other neighbors to share the load. While a node can be limited to only be 1 role at a time, which would be determined by the role morphogen that has the highest activation, it may still have high activation in other role morphogens which will hinder neighbors becoming this role due to its long range inhibition. To mitigate the chance of 1 node becoming high in multiple morphogens, the original morphogen equation (EQN 2) needs to be modified to take into account some global inhibition. The term global meaning across all role morphogens in a node, not across all nodes in a graph.

The global inhibition is added to each roles local inhibition and the extra pressure makes it harder for multiple morphogens to have high values on the one node. Multiple morphogens to have high values on the one node.

$$b_g = G(s_1 a_1^2 + s_2 a_2^2 + \ldots) \qquad \text{EQN 8}$$

In some embodiments, the extracted constant G provides inhibition dampening. Note that the source density and activation are from the same role, as opposed to some other equations where they are opposite. The reason for this is because our modified source density (EQN 3) already factors in for the supporting role influence by accounting for desire (EQN 6). Equation 1 is modified to include the global inhibition and to make activation and inhibition role specific.

$$\frac{\partial a_r}{\partial t} = \frac{s a_r^2 + C_a}{b_r + b_g} - d_a a_r + D_a \frac{\partial^2 a_r}{\partial x^2} \qquad \text{EQN 9}$$

A more thorough discussion of these equations may be found in "Embryonic Stream Processing Using Morphogens", Nature and Biologically Inspired Computing (NaBIC) 2010, K. Sabir and D. Lowe.

In some embodiments, each node in the system may connect to other nodes in a web. The processing load may be distributed across all of the nodes in the system, without requiring the use of a central server (i.e. decentralized). This may mean that the nodes are relatively lightweight, as no single node has to know how to do all of the processing required. Also, in some embodiments, the roles may be rotated between the nodes if needed (e.g. to save on wear-and-tear, or to maximize battery life, etc.).

In some embodiments, new nodes may only need the address of (or a connection to) one existing node in the system. From that, it may join the network, learn the genome, differentiate into a suitable role and start processing. Each of the new processing nodes may be configured to identify one or more tasks available to perform and to analyze one or more of the existing processing nodes to identify a most suitable task to perform.

In some embodiments, the inputs (i.e., sources) may be fixed (e.g. one or more sensors getting temperature), and/or receiving inputs served from a server, like SETI@home. Additionally and/or alternatively, the inputs could be related to the new nodes coming in (e.g. monitoring the vibration of your phone, when more phones are added to the network, the inputs increase).

Figure 4:
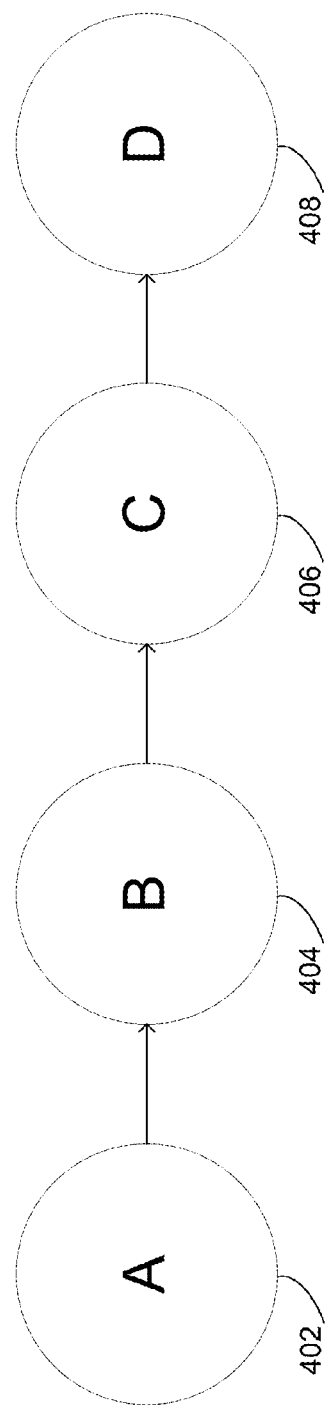
FIG. 4 depicts a dataflow graph consistent with the processes of the present disclosure.
Figure 5:
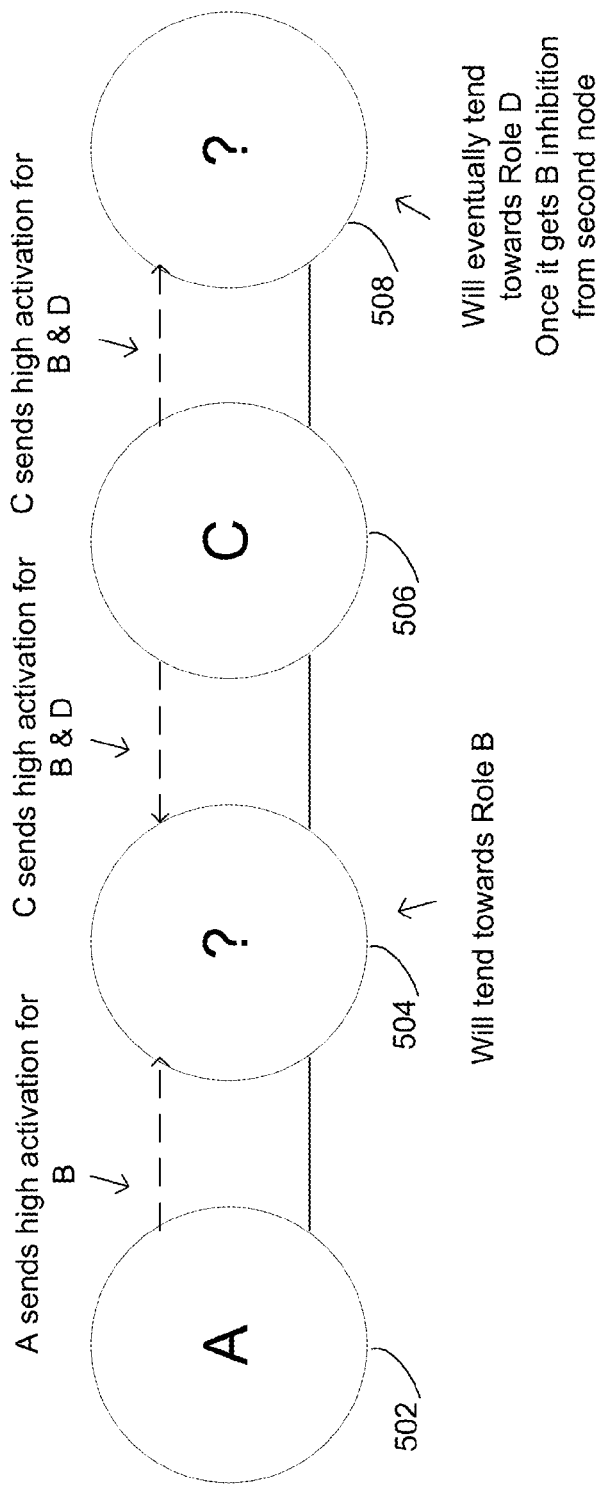
FIG. 5 depicts a dataflow graph consistent with the processes of the present disclosure.

Referring now to FIGS. 4-5, two diagrams (400, 500) depicting a streams dataflow graph are shown. Diagram 400 may include a number of nodes, for example, nodes 402 (A), 404 (B), 406 (C), and 408 (D). Any suitable number of nodes may be employed. Each node may correspond to a processor, which may be configured to perform a particular role. Information may pass between one or more of nodes 402-408. FIG. 5 shows how nodes 504 and 508 may differentiate into roles B and D to suit the genome (e.g., the dataflow graph) to maximize efficiency by reducing the distance between hops.

The Hierarchical Stream Process

In some embodiments, the method may include providing (100) a plurality of processing nodes each of said processing nodes configured to transmit and receive a stream of data. The method may also include providing (102) a genome including a hierarchical set of tasks that represent a hierarchical functional decomposition of one or more problem scenarios. The method may further include identifying (104), at each of the processing nodes, one or more tasks for a first genome level. The method may additionally include differentiating (106), at one or more of the plurality of processing nodes, into one or more tasks, based upon, at least in part, the first genome level. The method may further include grouping (108) a plurality of the processing nodes together to achieve a power level. The method may also include activating (110) a second genome level once the power level has been reached. The method may further include repeating (112) until one or more of the nodes differentiates into a further genome level.

As discussed above, the stream application may be represented by a data flow diagram and this inter-role relationship may make up the genome along with any specific requirements for roles (e.g. a role might require the node has a camera sensor as an input). The genome may be shared across all of the nodes in the system, and each node may autonomously differentiate into an appropriate role based on the roles of its neighborhood (e.g. its nearest nodes). Each of the plurality of processing nodes maintain One or more morphogen levels associated with its parent processing node.

In some embodiments, the teachings of the present disclosure may be applied to any number of suitable applications. Some of these may include, but are not limited to, distributed sensor networks, phone applications, mainframes or even smart dust. Here, the term "smart dust" may refer to one or more small sensors known as motes made from Micro Electro Mechanical Systems (MEMS) or Nano Electro Mechanical Systems (NEMS). These may be cheap, autonomous and small enough to be able to be painted onto walls.

In some embodiments, as the application becomes more complex, scalability issues may arise. For example, if the genome is 10 roles, then each node in the system will have a copy of the genome and its 10 roles so it may determine which one to differentiate to. However, as the genome gets more complex, say 10,000 roles (e.g. a MEMS application simulating a desktop computer on a wall, splitting into CPU, Memory, Storage, etc), then it may become unfeasible for each node to know the entire genome (especially when considering the memory constraints of a MEMS device).

Also, in some embodiments, if a node's neighbors have already all differentiated into the first 50 out of 10,000 roles, then it may be inefficient for that node to know the entire genome. It may be possible to optimize network traffic by having each node select nearby roles, as it is likely only going to differentiate into a possible first ~50-100 roles.

In some embodiments, the hierarchical embryonic stream process described herein may be used to break a particular genome into a hierarchy for embryonic computing where each node only knows a subset of the genome. For example, at the top of the genome hierarchy may be a generic process describing the whole system. The lower levels of the genome hierarchy may include very specific processes. Nodes may start at the top process and unify with neighboring nodes until they have enough power to trigger the next level of the genome at which point they may differentiate into the different roles at the lower genome level. In this way, each of the plurality of processing nodes may be in communication with a subsection of a genome.

In some embodiments, each genome level may have a minimum power requirement which may be needed by nodes that have taken on that role. Reaching a power level may be associated with obtaining a desired amount of processing power for a particular task. For this minimum power to be reached, a group of nodes may need to gather in 'unity' to all belong to that given role. Once this power requirement has been reached, then the next level of the genome under that role is triggered. As the lower levels are triggered, more processes may be available for the nodes to differentiate into, hence the nodes may specialize over time. This process may then repeat so the nodes may eventually evolve into a complex application.

In some embodiments, and apart from the benefits of memory management and application complexity scalability, the teachings of the present disclosure may make it simpler for the developer to comprehend how the system is operating through the use of information hiding. For example, each genome level may be broken down to a number of distinct roles which may be easier to comprehend then looking at a flat 10,000 role genome.

There are similarities found in biology through some genes being able to activate whole pages of other genes, in effect simulating information hiding. The hierarchical genome from a biological viewpoint is also discussed in the book: Gordon, R., The Hierarchical Genome and Differentiation Waves, Novel Unification of Development, Genetics and Evolution, Singapore: World Scientific Publ. Co., 1999 A. G. Desnitskii Biological Research Institute, St. Petersburg State University.

Figure 6:
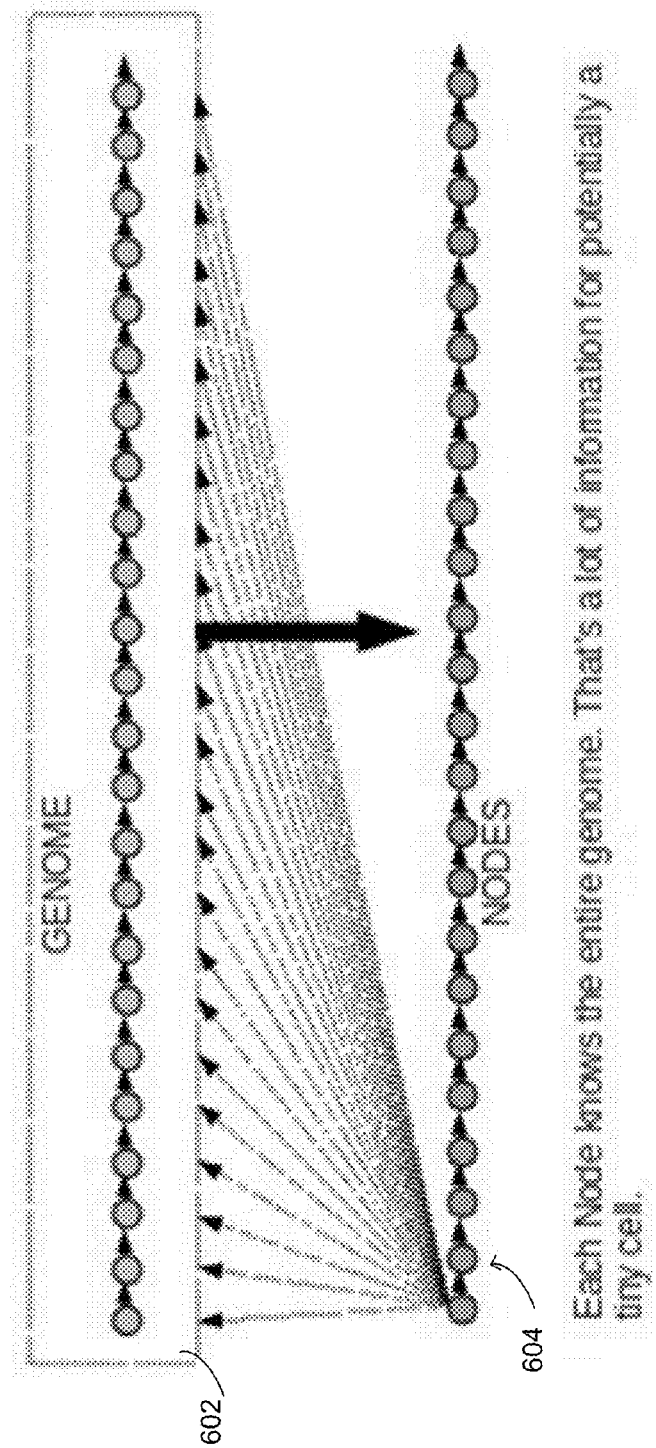
FIG. 6 depicts a dataflow graph consistent with the processes of the present disclosure.

Referring now to FIG. 6, an embodiment 600 is provided depicting a diagram where each node knows the entire genome. The top circles represent the genome data flow diagram 602. In this particular example, data flow diagram 602 is a trivial sequential diagram. The bottom nodes 604 may represent the actual nodes in the system (e.g., sensors, phones, motes, cells in a blue gene, etc).

Figure 7:
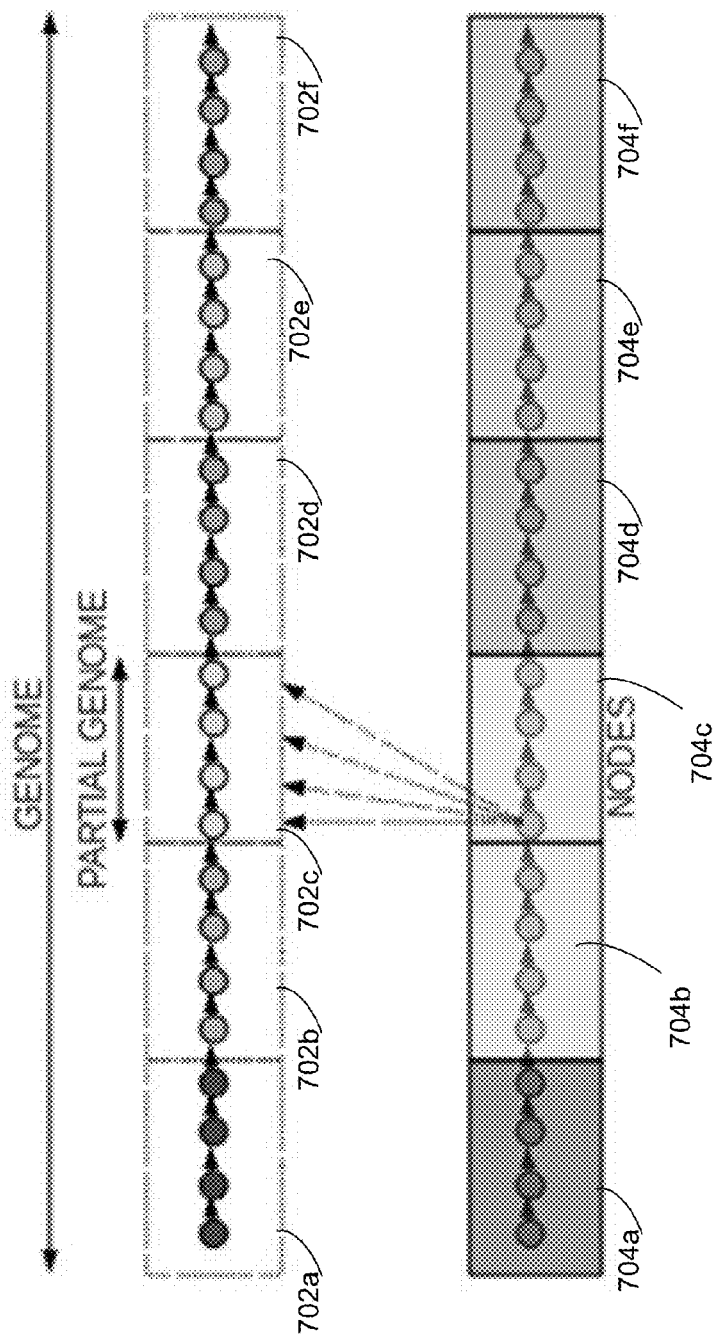
FIG. 7 depicts a hierarchical genome configuration consistent with the processes of the present disclosure.

Referring now to FIG. 7, a diagram 700 of an embodiment is provided depicting a hierarchical genome where each node only knows a subsection of what is relevant from the genome. For example, diagram 700 includes partial genomes or subsets 702a-f. Each node only knows its partial genome or subset, e.g., nodes 704c know partial genome 702c, nodes 704d know partial genome 702d, etc.

Figure 8:
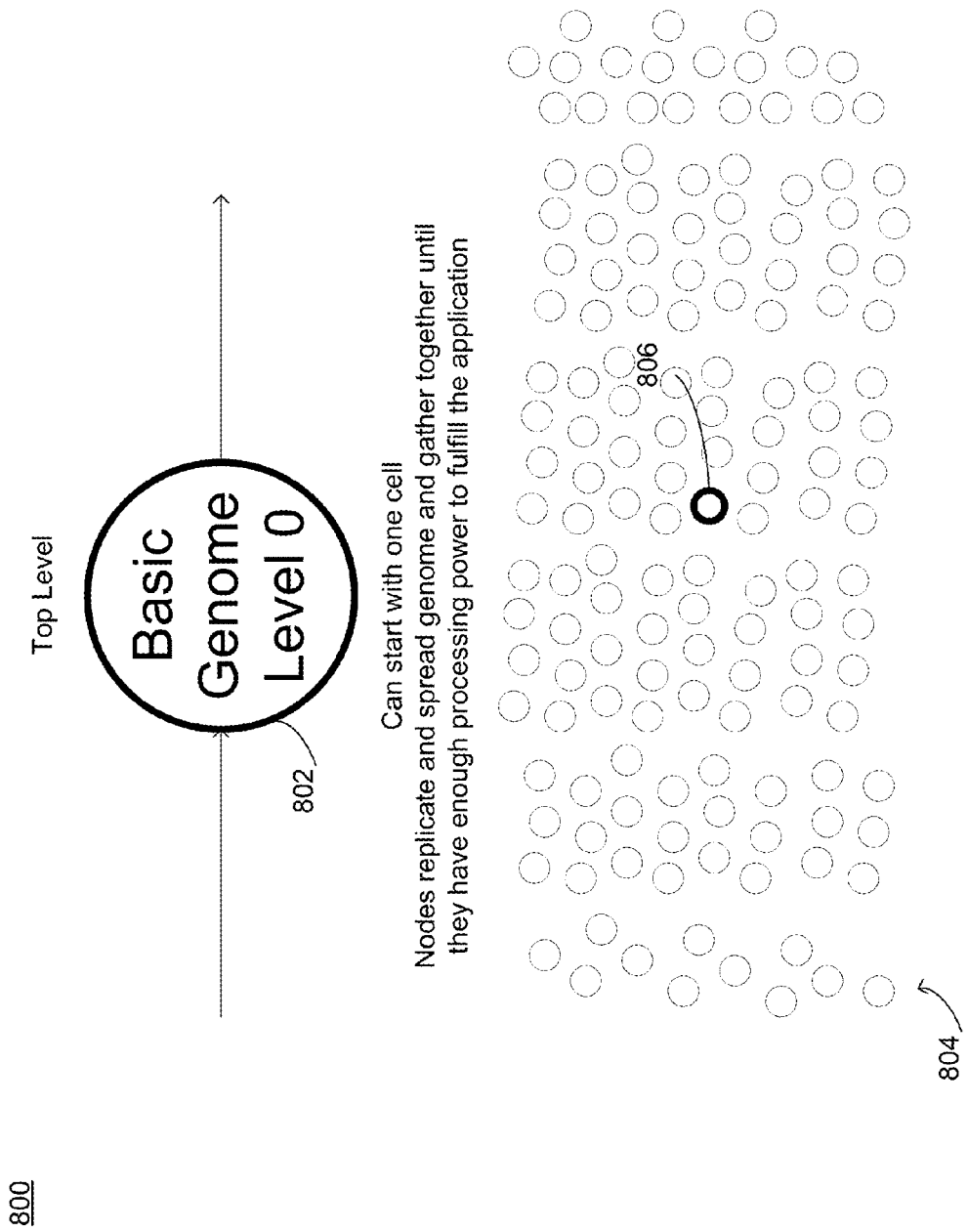
FIG. 8 depicts a diagram consistent with the processes of the present disclosure.
Figure 9:
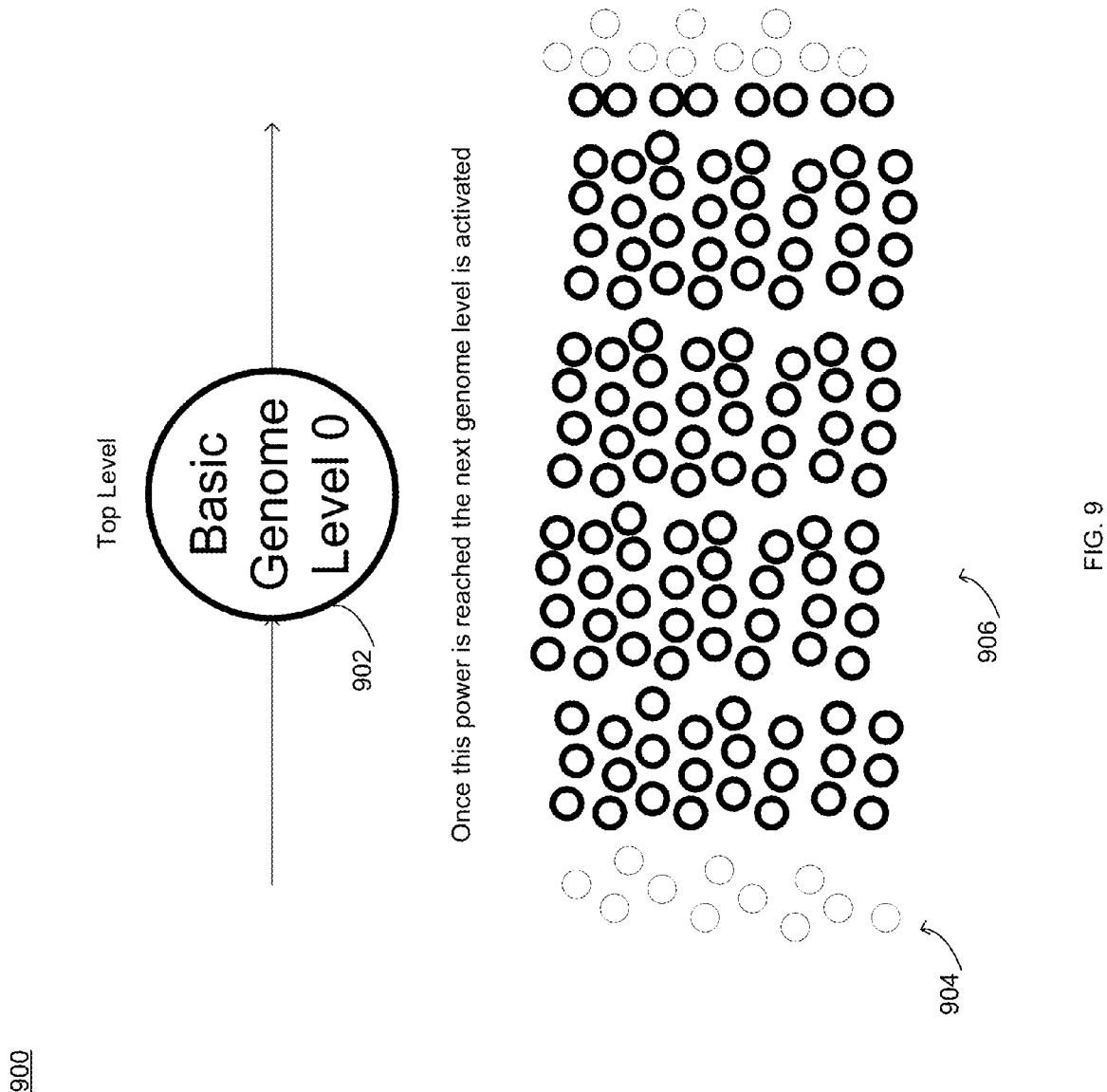
FIG. 9 depicts a diagram consistent with the processes of the present disclosure.

Referring now to FIGS. 8-11, a diagram 800 is provided depicting top level genome 802. In this particular embodiment, top level genome 802 appears as just one role. Diagram 800 also includes a number of undifferentiated nodes 804. Node 806 represents a node that has differentiated to the role of top level genome 802. As shown in FIG. 8, this may begin with one cell and individual nodes may replicate and spread the genome, gathering together until there is enough processing power to fulfill the application. In this way, and in accordance with the present disclosure, each individual node may receive a genome level, differentiate into roles from that genome level, gather the minimum power for a role by grouping together (e.g., unified group 906 shown in FIG. 9), and activate the next genome level for that role.

Figure 10:
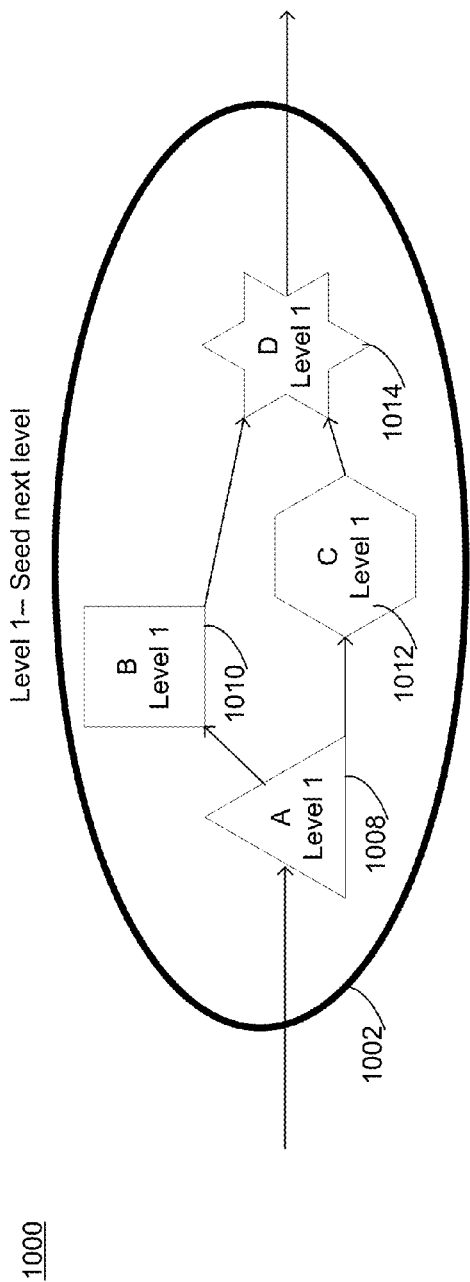
FIG. 10 depicts a diagram consistent with the processes of the present disclosure.
Figure 10:
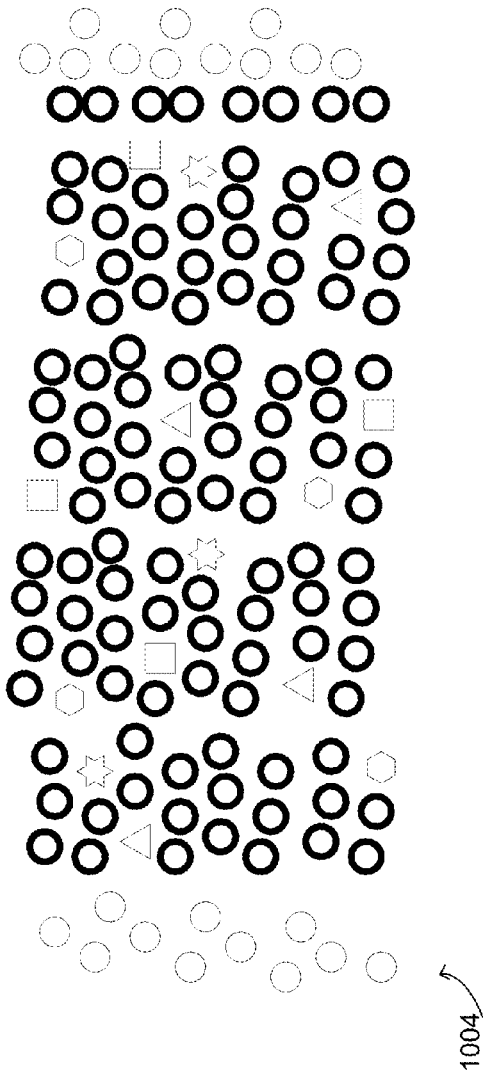

Referring now to FIG. 10, a diagram 1000 is provided depicting the transition to the next level genome 1002. In some embodiments, the hierarchical embryonic stream process 10 described herein may utilize quorum sensing as part of the grouping and decision making process. In this way, each individual component or node may have a means of assessing the number of other components or nodes that they interact with and may also have a standard response once a threshold number of components is detected.

Referring now to FIG. 10, diagram 1000 shows the evolution from the top level genome (e.g. basic genome level 0) to the next level. As shown in the figure, as the next level evolves it may differentiate into one or more sub-roles, as indicated by level 1 A 1004, level 1 B 1006, level 1 C 1008, and level 1 D 1010. Again, it should be noted that the teachings of the present disclosure may be utilized in a variety of applications. For example, in the smart dust scenario discussed above, level 1 A 1004 may correspond to a CPU, level 1 B 1006 may correspond to a hard drive, level 1 C 1008 may correspond to an application space, and level 1 D 1010 may correspond to some I/O.

Figure 11:
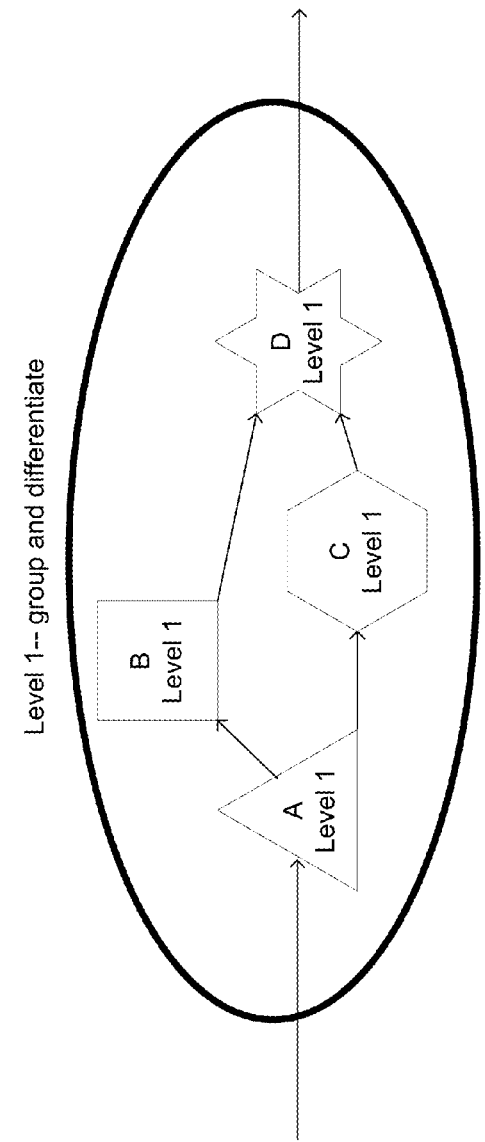
FIG. 11 depicts a diagram consistent with the processes of the present disclosure.
Figure 11:
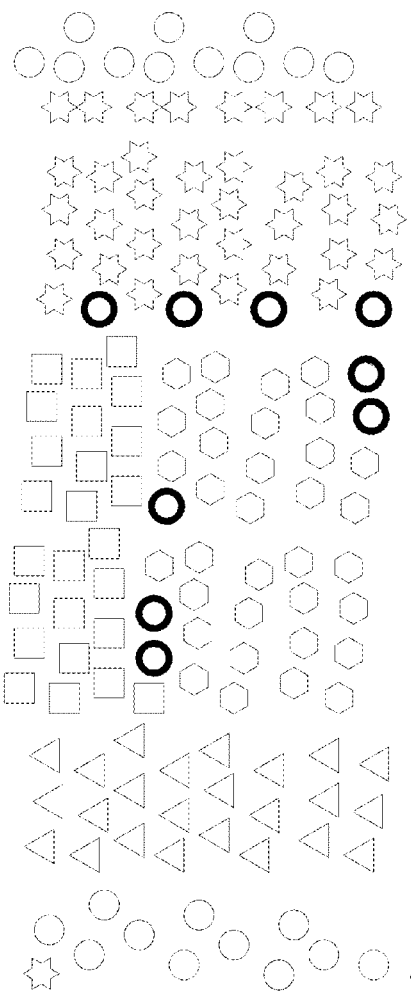
Figure 12:
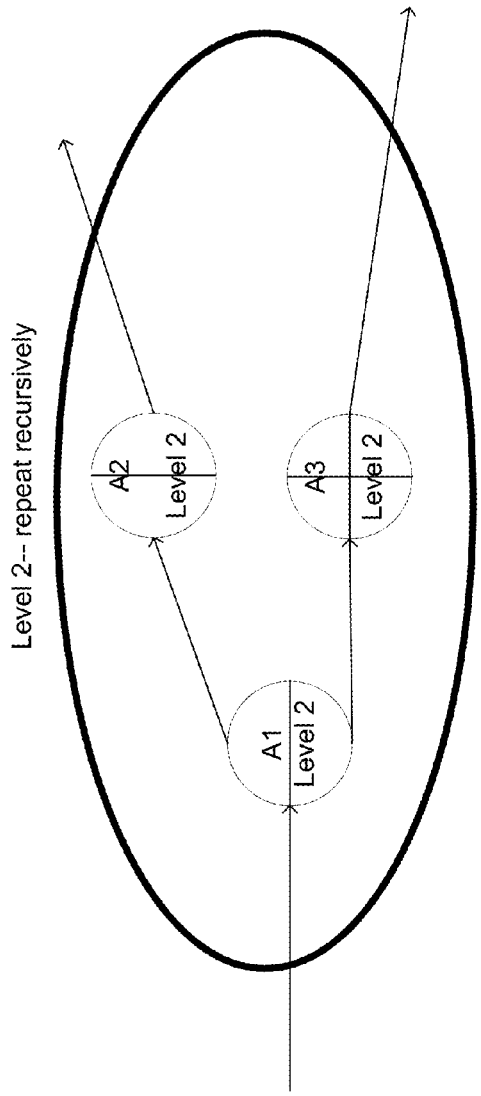
FIG. 12 depicts a diagram consistent with the processes of the present disclosure.
Figure 12:
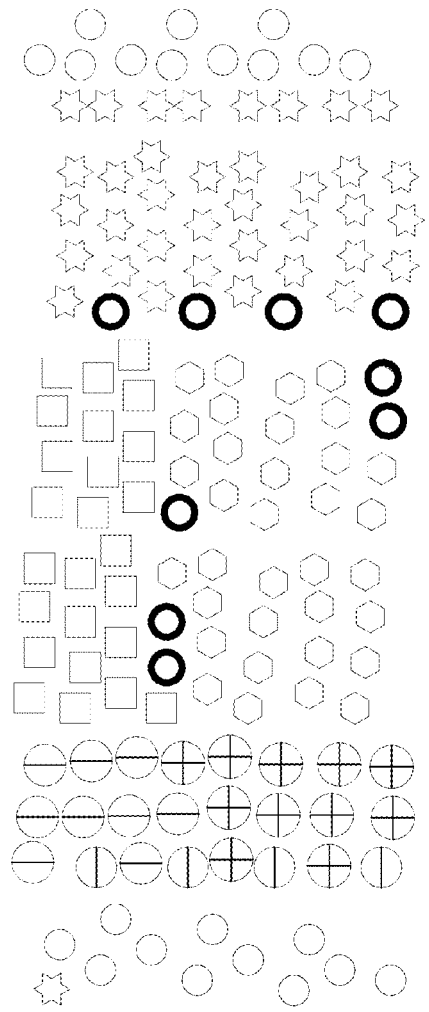

Referring now to FIG. 11, diagram 1100 shows the nodes grouping together and differentiating. In some embodiments, the nodes may group together to satisfy an existing genome level. Once any group has reached its desired power, the next genome may be activated for that particular group. FIG. 12 depicts a diagram 1200 showing an embodiment after the nodes continue to specialize. Each node may maintain morphogen levels for its parents, which were previously calculated as well as its current genome set. In some embodiments, each of the plurality of processing nodes may maintain one or more morphogen levels associated with its parent processing node. In some embodiments, the morphogen levels may be associated with at least one of activation and inhibition.

As discussed above, each possible role of the genome may have a morphogen pair (e.g., activation and inhibition). With a hierarchical genome, a node may be operating multiple roles, e.g., a top level role, a child role of that, a child role of that, etc. The higher level roles may continue to function after its child genome level has been triggered and may still follow the morphogenesis laws of auto-catalytic activation and long range inhibition. However, since they have reached a certain level of power and hence stability, they will not be re-differentiating as rapidly as the lower level roles.

In some embodiments, since the higher level roles still operate, there is a chance of high level load balancing between nodes that exist on the boundaries of child roles (e.g. for node failure or a change in input load). When a higher level role differentiates to load balance, then the existing child genome levels can be discarded as a new child genome level will be obtained.

Figure 13:
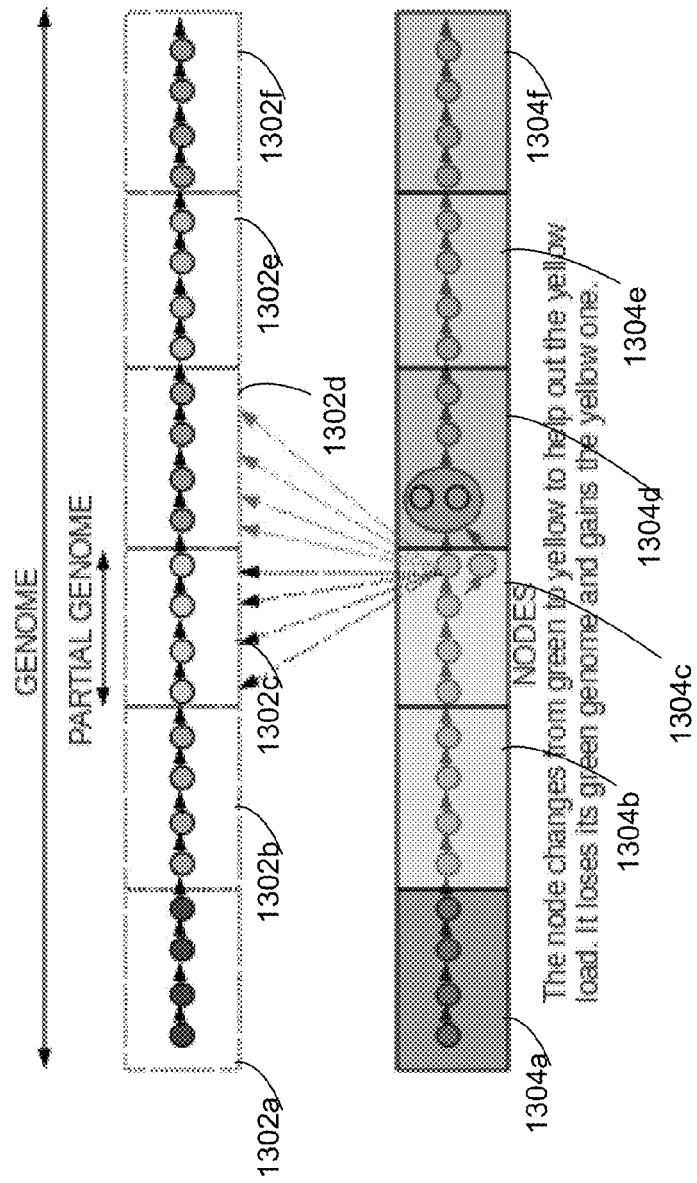
FIG. 13 depicts a diagram consistent with the processes of the present disclosure.

Referring now to FIG. 13, a diagram 1300 is depicted showing load balancing between one or more of the plurality of processing nodes. More specifically, diagram 1300 shows roles 1304c being under load so they get help from the roles 1304d. A node from 1304d becomes a node from 1304c and it discards its old genome level (see the lines connecting 1304c and 1302d) and obtains the new genome level (see the lines from 1304c to 1302c).

Figure 14:
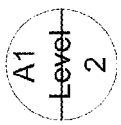
FIG. 14 depicts a table consistent with the processes of the present disclosure.

Referring now to FIG. 14, a table 1400 is provided including a description of morphogen levels on a node that has differentiated into A1 from FIG. 12. At each level of the genome, some nodes (known as genome store nodes) may have the task of holding all of the sub genome levels. This way, each node may only need to know the current genome level of roles for possibilities of what it could differentiate into. Once the genome level's power has been triggered, then the next genome level is retrieved from the storage nodes, and the nodes may differentiate to satisfy the new level. Once nodes have unified to gather enough power for the child genome level, then new genome store nodes are created out of these unified nodes that may hold the child genome level and all its children genome levels.

Figure 15:
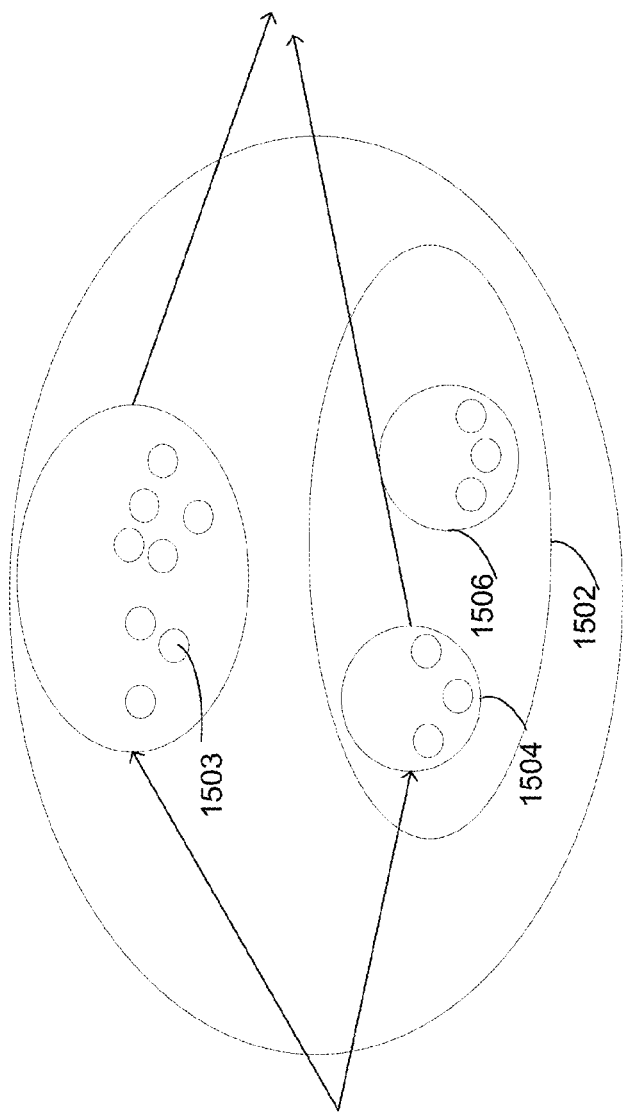
FIG. 15 depicts a diagram consistent with the processes of the present disclosure.

Referring now to FIG. 15, a diagram 1500 is provided depicting an embodiment including a meta genome level operating system (OS) 1502. In some embodiments, meta genome level OS 1502 may be created at every genome level. Meta genome level OS 1502 may provide a datastore to hold the entire genome and to keep track of input and output node identities. In some embodiments, some nodes in a genome level may be set aside to keep track of all inputs and outputs IDs in the genome level, known as I/O store nodes 1504. This redundancy may cover communication between the genome levels and allow for protection in the event that the existing nodes handling input and output fail. The genome store nodes 1506 and the I/O store nodes 1504 together may be seen as metadata for a genome level and may act like a simple operating system for that level. This type of configuration may be used, for example, if the genome is too large for a given device. In this way, a distributed database may be used for storage purposes (e.g. a few nodes may store the genome). The genome roles for the current level 1503 may be in communication with I/O store nodes 1504 and genome store 1506.

The Totipotent Morphogenic Stem Cell Process

In some embodiments, issues may arise concerning load balancing and robustness in a morphogenic system. For example, when a system stabilizes, a given node may have a high activation for its current role, and a high inhibition for all the roles it is not. When a node fails, there may be a delay in when the inhibition on nearby nodes can decay to a low enough level that another node can take up this role. Also, the other nodes may already be busy doing their own roles. In this particular case, if one is to take up the role of the node that died, then its own role may need to be shuffled to other nodes. The restructuring of many nodes roles may be inefficient and possibly slow for the system to reach stability again.

Nature accounts for cell robustness through the use of stem cells that are toti-potent, meaning they can differentiate into any type of cell. In this way, in some embodiments, the method may include providing a plurality of processing nodes each of said processing nodes configured to transmit and receive a stream of data. The method may further include restricting a subset of the plurality of processing nodes from differentiating into a role. The method may also include identifying a failure at one of the processing nodes and replacing the failed node with one of the processing nodes from the restricted subset.

In other words, the totipotent process described herein may restrict some (e.g. 10%) of the nodes from differentiating into roles, and these nodes may wait for node failure, and then immediately differentiate into the required role. These nodes in waiting may be similar to stem cells in adult organisms, where they delay differentiating to handle failover. As used herein, these nodes in the stream processing domain may be referred to as morphogenic stem cells ("MSC"). The benefit of using MSC is that because they are not accepting inhibition through diffusion, they may rapidly differentiate once they are required to handle the failover. In some embodiments, morphogenesis may be used to determine the spatial placement of the MSC in the system.

While the concept of redundancy for self-healing is known in embryonic systems (see a hardware example in "Reliability Analysis in Self-Repairing Embryonic Systems", Cesar Ortega and Andy Tyrrell, Department of Electronics University of York), the present disclosure uses morphogenesis to determine which nodes will become stem cells. The benefit of using morphogenesis is that the MSC placement may not be pre-fixed, and it may fluctuate depending on the genome size, the clustering coefficient (e.g., how 'dense' the network is), the critical nature of the role and the average failure time.

Also, using morphogenesis may allow for new MSC's to be created from the most under-utilized roles. Therefore, the system is self-healing due to the use of MSC, and its repair mechanism is also self-healing (e.g., in the creation of new MSC's).

In some embodiments, the MSC may spatially separate by using morphogenic equations that support self-catalytic activation and long range inhibition. The equations for morphogenic behavior for spatial separation are described above in Equations 1 and 2. (see Sabir, K. and Lowe, D., "Embryonic stream processing using morphogens", Nature and Biologically Inspired Computing (NaBIC), 2010 Second World Congress on, vol., no., pp. 603-610, 15-17 Dec. 2010). In this way, a restricted subset of processing nodes may be spatially separated throughout a plurality of nodes. In some embodiments, spatial separation may be based upon the activation level and/or the inhibition level.

In some embodiments, the activation constant Ca from Equation 1 may be influenced by various criteria, including, but not limited to, genome size, the clustering coefficient (e.g., how 'dense' the network is), the critical nature of the role and the average failure time. For example, if a role is critical, it may have a higher density of MSC's present in its neighborhood.

In some embodiments, the morphogens used for MSC and the role morphogens detailed above may differ in that while role morphogens are influenced by other role morphogens, the MSC morphogens are completely independent of the role morphogens. This may allow it to have no pre-existing inhibition at the time it needs to differentiate for failover. In biological terms, it is simulating the instant birth of a new cell in biological terms.

In some embodiments, once an MSC has been activated for failover, it may act like a normal new node in the morphogenesis process, so if a role has disappeared, then there may be a high desire for that role promoting the MSC to differentiate to that role. Also, once an MSC has differentiated, then that may create a demand for a new MSC in that area. While the MSC morphogens are not affected by role morphogens, they may be affected by a nodes current load. This may stop a node under heavy load from stopping its work and differentiating into an MSC, and it may promote nodes under light load to be candidates to become a new MSC. In other words, an under utilized node may be added to the subset after a failed node has been replaced.

Creating demand for a new MSC seems like it is revisiting the original problem of inefficient restructuring of node's roles. However, it differs in that MSC may allow for rapid differentiation due to no pre-existing inhibition. This extra redundancy may allow for the application to respond rapidly to failover. Additionally and/or alternatively, the most under-utilized node in the area may become the new MSC, and since there may be no dependencies between role morphogens and MSC's, there may be less 'role shuffling' required as there are no desired neighbors for a MSC. The process to replenish a MSC is not as time critical as normal failover.

In some embodiments, MSC's may be able to determine and/or identify when a fail has occurred due to the excess of the desire morphogen and lack of power for a given role in the system. In this way, enough MSC's need to be present in the system so the differentiated nodes can adequately handle the load. This architecture may also allow for MSC's to differentiate to help in times of peak load, where the existing processing power is not enough.

The Multipotent Morphogenic Stem Cell Process

While the totipotent MSC's described above could exist and function within a hierarchical genome, there is a chance that due to the number of roles co-existing per node (including the parent roles and the chosen differentiated child role), it could be possible that a high demand for stem cells for one genome level may reduce the robustness of other genome levels as the stem cells are already used up. This may hinder a genome level's ability to act autonomously as failures in other genome levels may directly affect its ability to self-heal.

In some embodiments, the multipotent morphogenic stem cell process described herein may add capability to the hierarchical genome concept by adding MSC for each level of the genome. Where instead of each MSC being totipotent (i.e., being able to differentiate to any role), each genome level may have its own MSC's. So each MSC at each genome level may only differentiate into roles for that genome level (meaning the MSC is multipotent).

In some embodiments, the method may include providing a plurality of processing nodes in a hierarchical genome having a plurality of levels, wherein each of said processing nodes is configured to transmit and receive a stream of data. The method may further include restricting a subset of the plurality of processing nodes from differentiating into a role within each level of the hierarchical genome. The method may also include identifying a failure at one of the processing nodes and replacing the failed node with one of the processing nodes from the restricted subset.

In some embodiments, the MSC's may act as a restricted subset of the processing nodes that may be spatially separated within each level of the hierarchical genome. This spatial separation may be based upon one or more of an activation level and an inhibition level from the parent genome level. After the failed node has been replaced a new node may be added to the restricted subset, thus supplying a replacement MSC. This added node may be an under-utilized, or relatively under-utilized node. In some embodiments, each genome level may maintain a separate restricted subset of nodes configured to handle node failure for the genome level. The processes described herein may be configured to identify a failure by determining one or more of a desire level and a power level. Each unrestricted node may include an activation level and an inhibition level as is discussed above.

In biology, the stem cell differentiation potency is classified in order of decreasing potency as totipotent, pluripotent, multipotent, oligopotent and unipotent. Since streams processing applications are diverse in both application complexity and topology size, the present disclosure shall arbitrarily call all MSC in a hierarchical genome as multipotent, as they all operate in the same way, in that they can only differentiate into roles from their genome level. (Other naming options would be pluripotent or oligopotent).

In some embodiments, the distribution of multipotent MSC may be similar to that described above with regards to totipotent MSC using self catalytic activation and long range inhibition. However, a genome level may have its own distributions of MSC's. In some embodiments, the trigger for a multipotent MSC to activate may be the same as a totipotent MSC, that is large desire and little power for a particular role (in this case, a role limited to its genome level).

In some embodiments, a multipotent MSC may not accept role morphogens from its own genome (or child genome) level. However, it may accept role morphogens from its parent genome level. This may allow the MSC to come pre-differentiated to its parent genome level so it can help its own genome level immediately when required.

Referring now to FIGS. 16-22, a series of diagrams are provided depicting various embodiments of the multipotent MSC process. In the diagrams, the top dataflow datagram refers to a particular genome level for a hierarchical genome. The bottom group of circles represents the actual topology, where the color reflects the role chosen for that node. Multipotent MSC's even work for the top genome level (though in a trivial manner) as FIGS. 16-18 describe.

Figure 16:
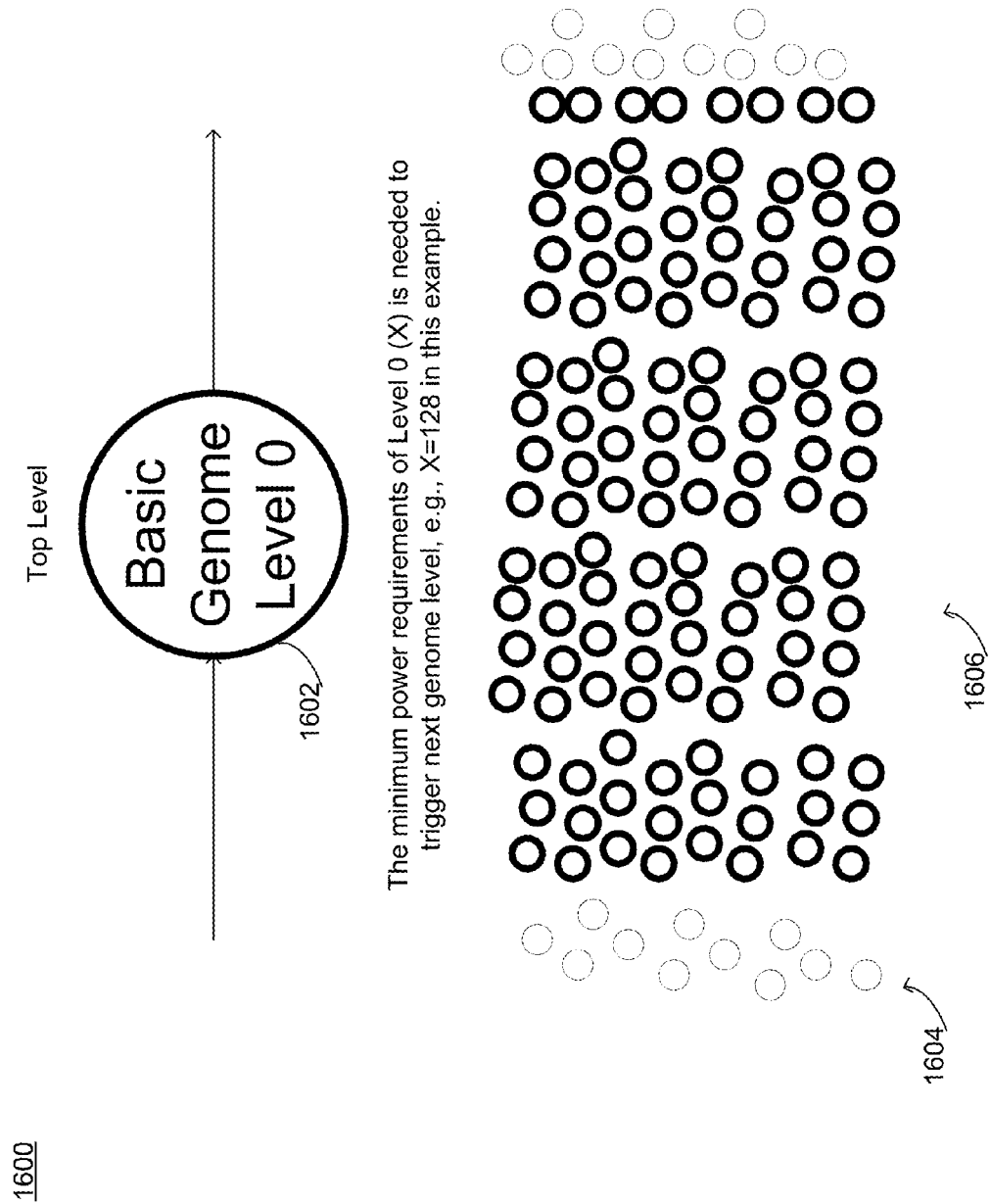
FIG. 16 depicts a diagram consistent with the processes of the present disclosure.
Figure 17:
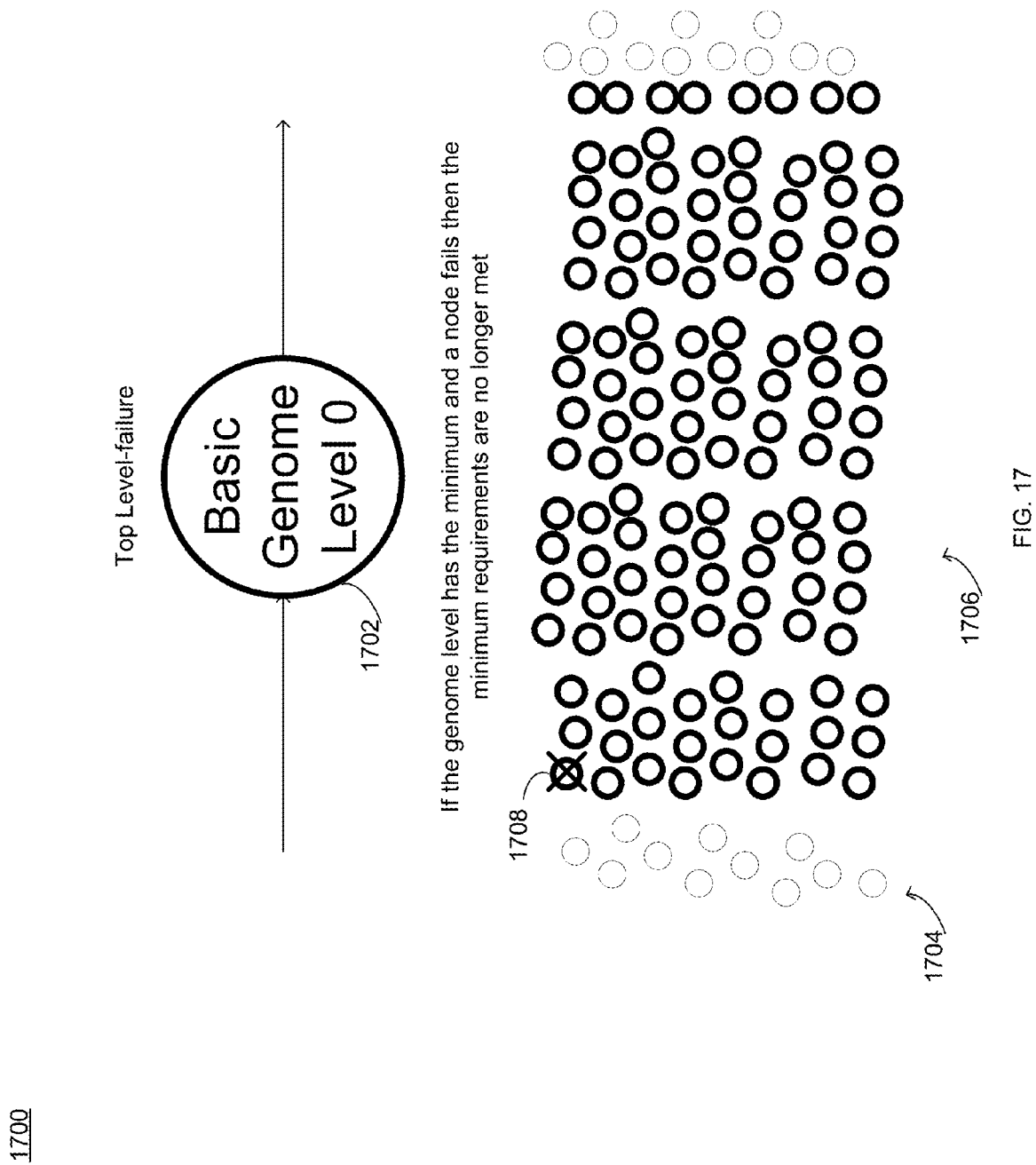
FIG. 17 depicts a diagram consistent with the processes of the present disclosure.
Figure 18:
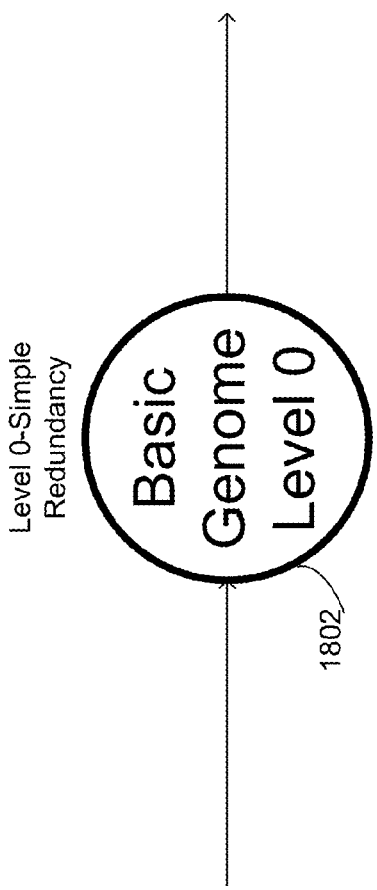
FIG. 18 depicts a diagram consistent with the processes of the present disclosure.
Figure 18:
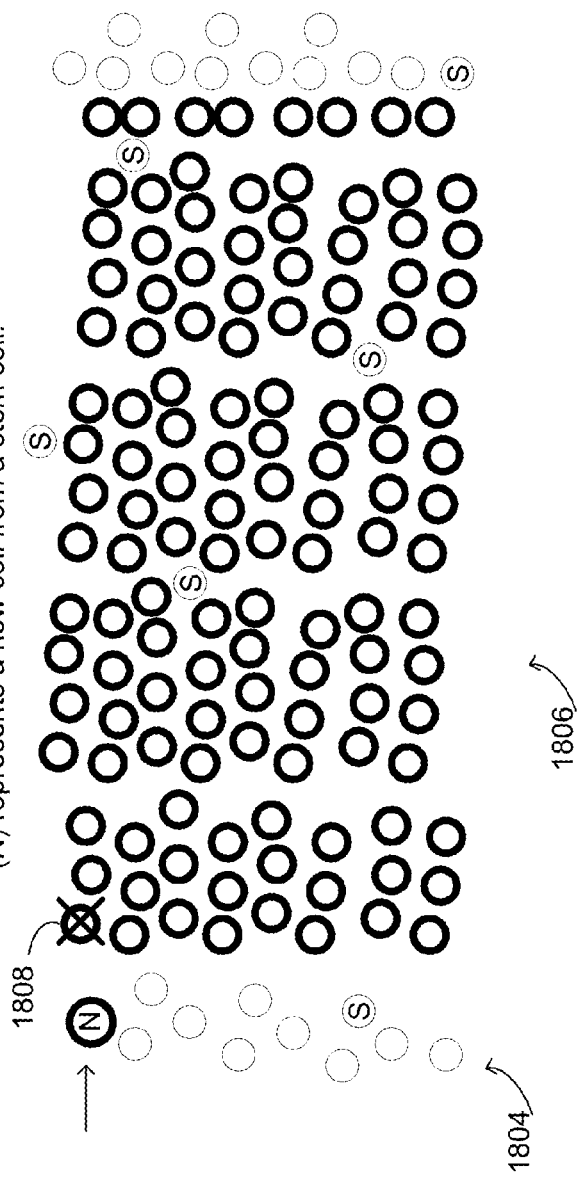

FIG. 16 depicts a diagram 1600 showing a basic genome level 0. In order to trigger the next genome level the minimum power requirements may need to be met. In this particular example, the minimum power requirement is 128. Once the minimum power requirements have been met, upon the failure of a node the minimum requirements are no longer satisfied as is shown in FIG. 17. However, if stem cells were also part of the minimum requirements calculation, then redundancy is built in. In this particular example, there may be only one type of role the MSC can differentiate into. These may be referred to as Level 0 stem cells ("S") as is shown in FIG. 18. Here, ("N") may represent a new cell from a stem cell.

Figure 19:
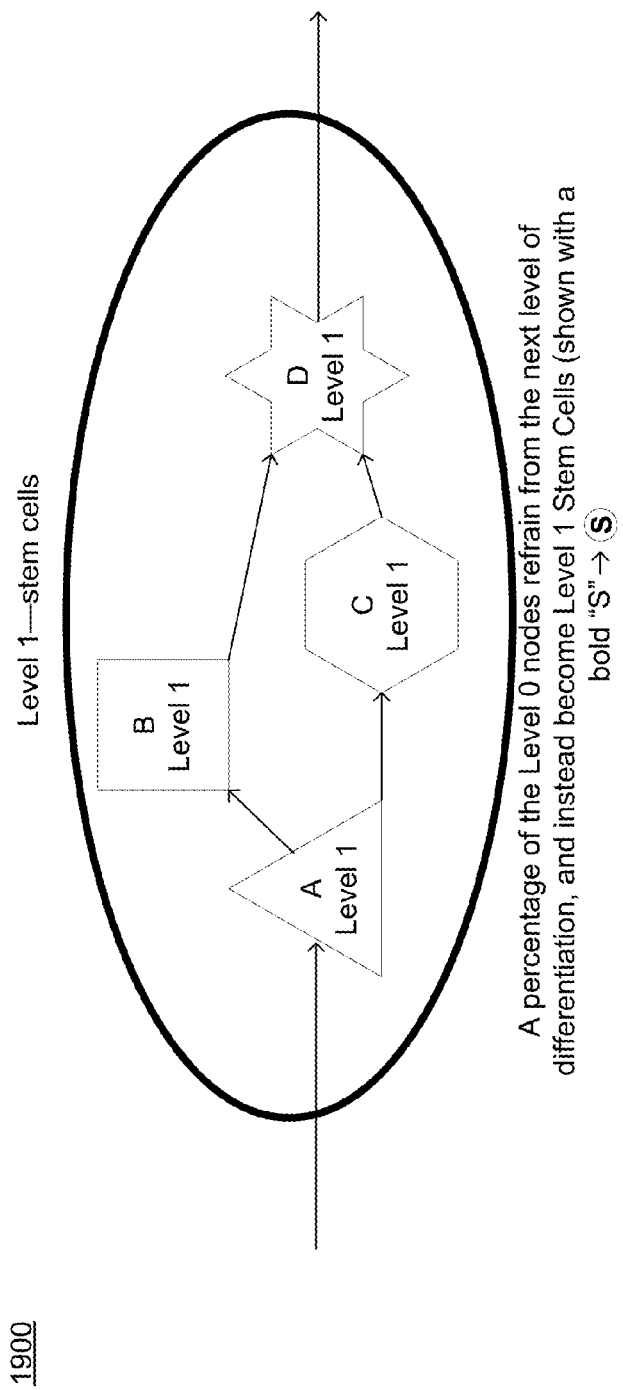
FIG. 19 depicts a diagram consistent with the processes of the present disclosure.
Figure 19:
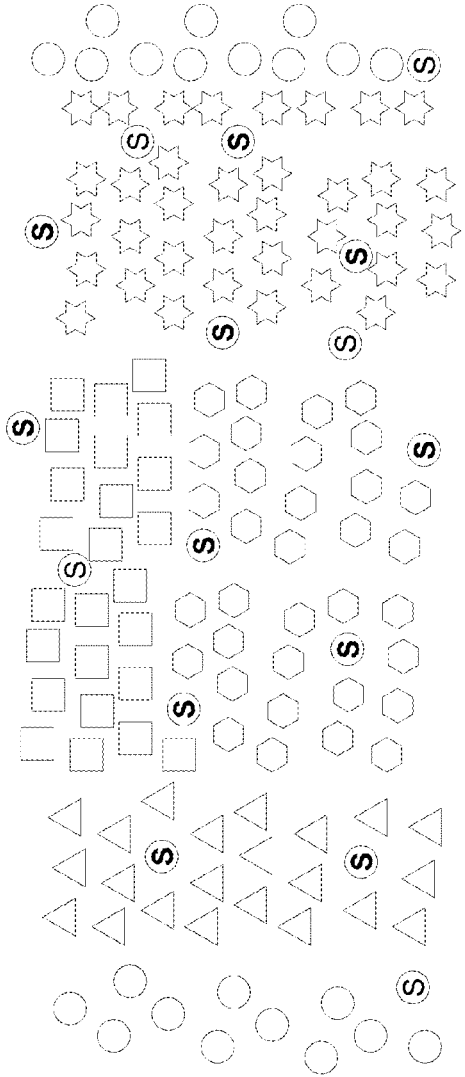
Figure 20:
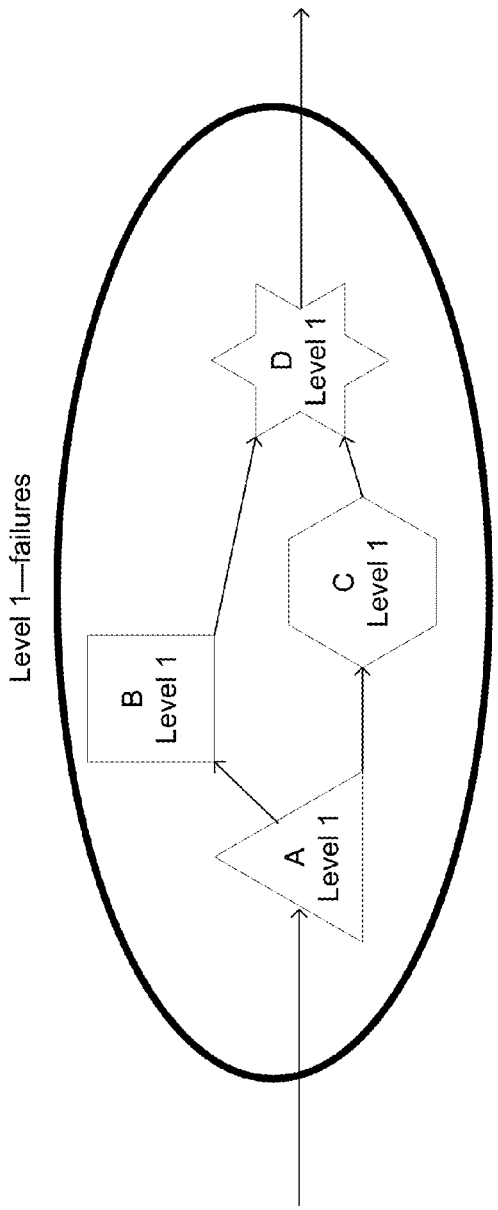
FIG. 20 depicts a diagram consistent with the processes of the present disclosure.
Figure 20:
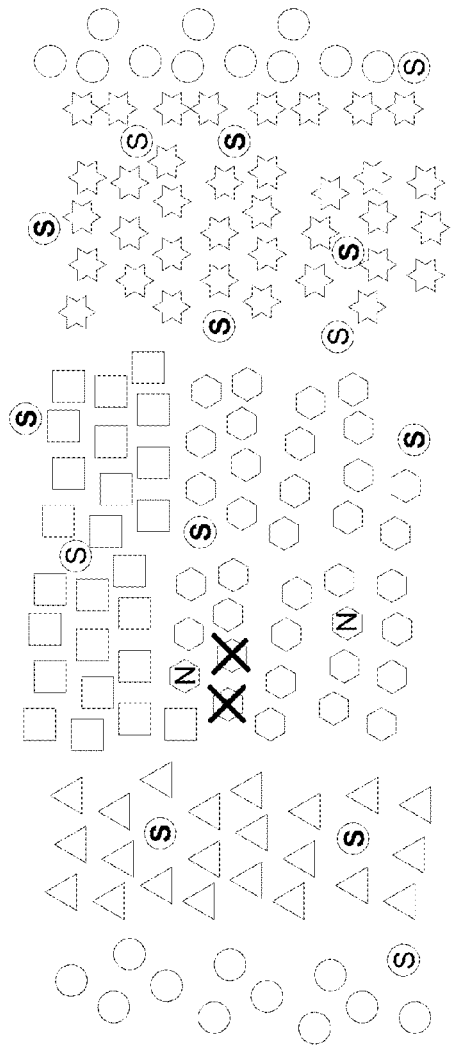

Referring now to FIGS. 19-20, a diagram 1900 is shown depicting the next genome level (i.e. Level 1). As shown in the Figure, at the next genome level (i.e., Level 1), both types of stem cells are in operation, namely, Level 0 Stem cells and Level 1 stem cells. In some embodiments, a percentage of the Level 0 nodes may refrain from the next level of differentiation, and instead become Level 1 stem cells. FIG. 20 depicts a diagram 2000 showing a failure of one of the nodes, at this point a Level 1 stem cell may replace the failed node. In some embodiments, the Level 1 stem cells may not receive the Level 1 role morphogens (i.e., A, B, C, D) however they may receive the Level 0 role morphogens.

Figure 21:
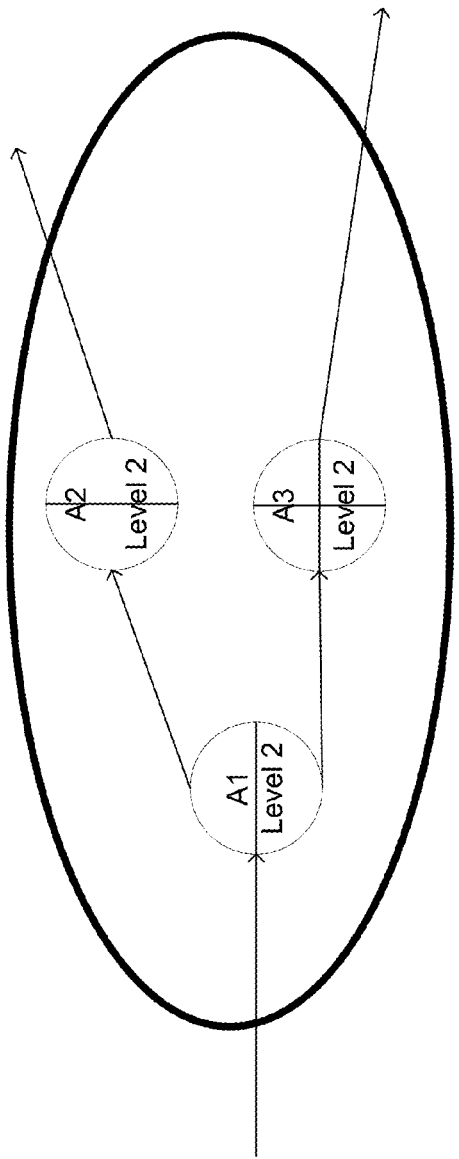
FIG. 21 depicts a diagram consistent with the processes of the present disclosure.
Figure 21:
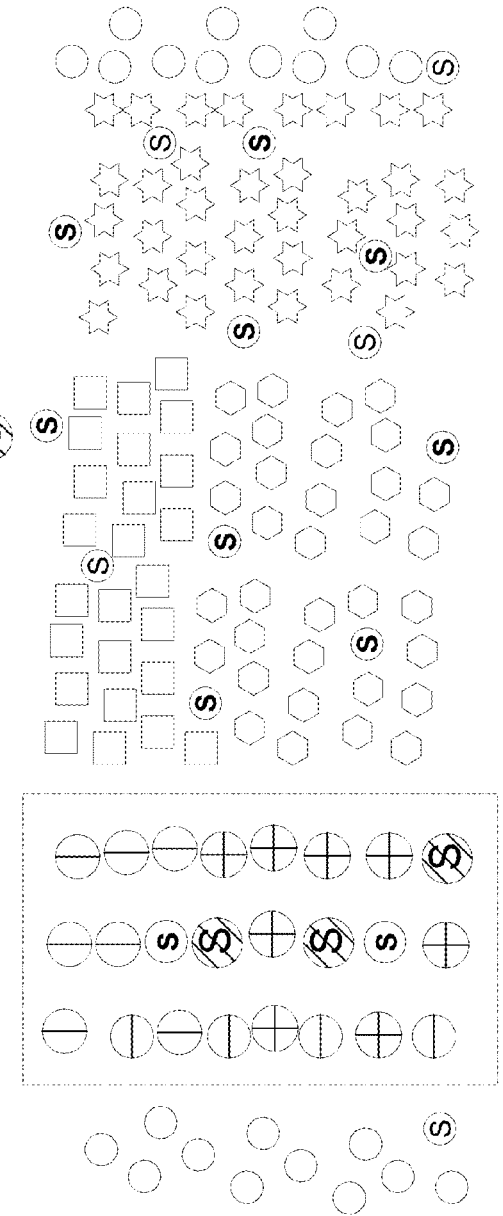
Figure 22:
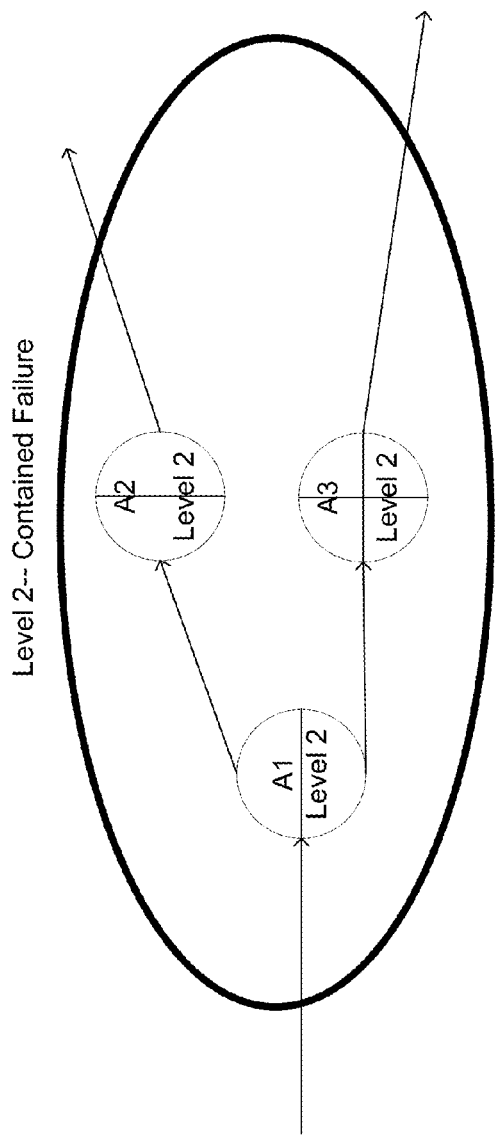
FIG. 22 depicts a diagram consistent with the processes of the present disclosure.
Figure 22:
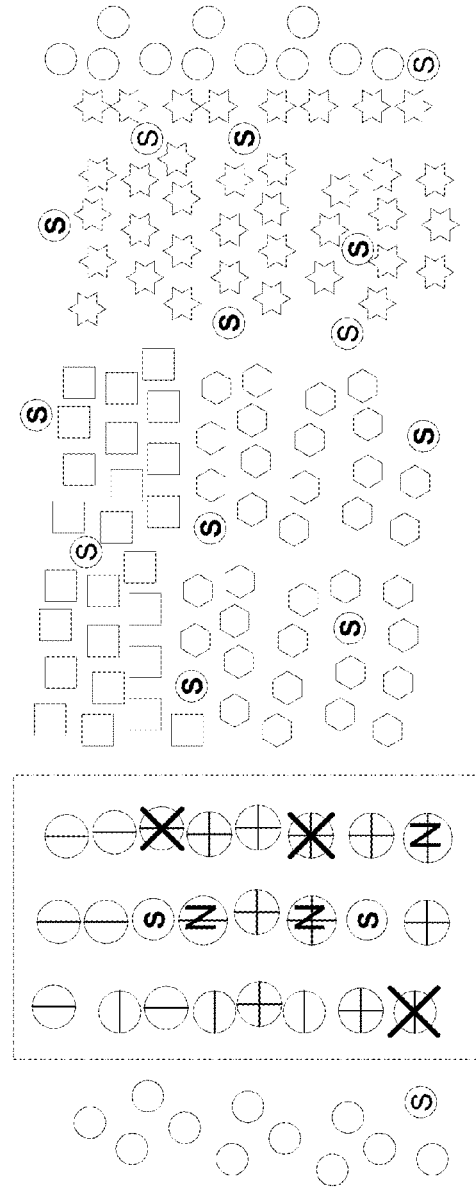

Referring now to FIGS. 21-22, a diagram 2100 is shown depicting the next genome level (i.e. Level 2). In some embodiments, the Level 2 stem cells for A may not receive Level 2 role morphogens (i.e., A1, A2, A3) however they may receive the Level 0 & Level 1 (i.e., A, B, C, D) role morphogens. This means that as soon as there is a failure in Level 2 for A (e.g. A1 dies) then there is a new cell (formerly a stem cell) that is already differentiated to A, yet it has no A1 inhibition to slow it down. These two criteria will ensure a rapid differentiation to replace the dead A1. FIG. 22 depicts a diagram 2200 showing a contained failure. The failure shown in FIG. 22 may temporarily use up all Level 2 stem cells for A, however, it may not directly effect on the self-healing capabilities of Level 1 roles, or of other Level 2 roles for B, C, and D.

As will be appreciated by one skilled in the art, aspects of the present invention may be embodied as a system, apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java™, Smalltalk™, C++ or the like and conventional procedural programming languages, such as the "C" programming language or similar programming languages. The program code may execute entirely on the user's computer (i.e., a client electronic device), partly on the user's computer, as a stand-alone software package, partly on the user's computer and partly on a remote computer or entirely on the remote computer or server (i.e., a server computer). In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention may be described with reference to flowchart illustrations and/or block diagrams of methods, apparatus (systems) and/or computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures may illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Further, one or more blocks shown in the block diagrams and/or flowchart illustration may not be performed in some implementations or may not be required in some implementations. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

A number of embodiments and implementations have been described. Nevertheless, it will be understood that various modifications may be made. Accordingly, other embodiments and implementations are within the scope of the following claims.

What is claimed is:

1. A computer-implemented method for de-centralized stream processing, the method comprising:
    providing a plurality of processing nodes each of said processing nodes configured to transmit and receive a stream of data;
    providing a genome including a hierarchical set of tasks that represent a hierarchical functional decomposition of one or more problem scenarios;
    identifying, at each of the processing nodes, one or more tasks for a first genome level;
    differentiating, at one or more of the plurality of processing nodes, into one or more tasks, based upon, at least in part, the first genome level;
    grouping a plurality of the processing nodes together to achieve a power level;
    activating a second genome level once the power level has been reached; and
    repeating until one or more of the nodes differentiates into a further genome level.

2. The method of claim 1, wherein grouping utilizes, at least in part, quorum sensing.

3. The method of claim 1, wherein each of the plurality of processing nodes is in communication with a subsection of a genome.

4. The method of claim 1, wherein reaching a power level is associated with obtaining a desired amount of processing power for a particular task.

5. The method of claim 1, wherein each of the plurality of processing nodes maintains one or more morphogen levels associated with its parent processing node.

6. The method of claim 5, wherein the morphogen levels are associated with at least one of activation and inhibition.

7. The method of claim 1, further comprising:
    load balancing between one or more of the plurality of processing nodes.

8. A computer program product residing on a computer readable storage medium having a plurality of instructions for de-centralized stream processing, which, when executed by a processor, cause the processor to perform operations comprising:
    providing a genome including a hierarchical set of tasks that represent a hierarchical functional decomposition of one or more problem scenarios;
    identifying, at each of the processing nodes, one or more tasks for a first genome level;
    differentiating, at one or more of the plurality of processing nodes, into one or more tasks, based upon, at least in part, the first genome level;
    grouping a plurality of the processing nodes together to achieve a power level;
    activating a second genome level once the power level has been reached; and
repeating until one or more of the nodes differentiates into a further genome level.

9. The computer program product of claim 8, wherein grouping utilizes, at least in part, quorum sensing.

10. The computer program product of claim 8, wherein each of the plurality of processing nodes is in communication with a subsection of a genome.

11. The computer program product of claim 8, wherein reaching a power level is associated with obtaining a desired amount of processing power for a particular task.

12. The computer program product of claim 8, wherein each of the plurality of processing nodes maintains one or more morphogen levels associated with its parent processing node.

13. The computer program product of claim 12, wherein the morphogen levels are associated with at least one of activation and inhibition.

14. The computer program product of claim 8, further comprising:
    load balancing between one or more of the plurality of processing nodes.

15. A computing system for de-centralized stream processing comprising:
    at least one processor;
    at least one memory architecture coupled with the at least one processor;
    a first software module executable by the at least one processor and the at least one memory architecture, wherein the first software module may be configured to provide a plurality of processing nodes each of said processing nodes configured to transmit and receive a stream of data;

a second software module executable by the at least one processor and the at least one memory architecture, wherein the second software module may be configured to provide a genome including a hierarchical set of tasks that represent a hierarchical functional decomposition of one or more problem scenarios;

a third software module executable by the at least one processor and the at least one memory architecture, wherein the third software module may be configured to identify, at each of the processing nodes, one or more tasks for a first genome level;

a fourth software module executable by the at least one processor and the at least one memory architecture, wherein the fourth software module may be configured to differentiate, at one or more of the plurality of processing nodes, into one or more tasks, based upon, at least in part, the first genome level;

a fifth software module executable by the at least one processor and the at least one memory architecture, wherein the fifth software module may be configured to group a plurality of the processing nodes together to achieve a power level;

a sixth software module executable by the at least one processor and the at least one memory architecture, wherein the sixth software module may be configured to activate a second genome level once the power level has been reached; and a seventh software module executable by the at least one processor and the at least one memory architecture, wherein the seventh software module may be configured to repeat until one or more of the nodes differentiates into a further genome level.

16. The computing system of claim 15, wherein grouping utilizes, at least in part, quorum sensing.

17. The computing system of claim 15, wherein each of the plurality of processing nodes is in communication with a subsection of a genome.

18. The computing system of claim 15, wherein reaching a power level is associated with obtaining a desired amount of processing power for a particular task.

19. The computing system of claim 15, wherein each of the plurality of processing nodes maintains one or more morphogen levels associated with its parent processing node.

20. The computing system of claim 19, wherein the morphogen levels are associated with at least one of activation and inhibition.

\* \* \* \* \*